(12) United States Patent
Hauger et al.

(10) Patent No.: US 10,274,714 B2
(45) Date of Patent: Apr. 30, 2019

(54) SURGICAL MICROSCOPE FOR GENERATING AN OBSERVATION IMAGE OF AN OBJECT REGION

(71) Applicant: Carl Zeiss Meditec AG, Jena (DE)

(72) Inventors: Christoph Hauger, Aalen (DE); Guenter Meckes, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 214 days.

(21) Appl. No.: 15/242,134

(22) Filed: Aug. 19, 2016

(65) Prior Publication Data

US 2016/0357003 A1 Dec. 8, 2016

Related U.S. Application Data

(63) Continuation of application No. PCT/EP2015/053552, filed on Feb. 19, 2015.

(30) Foreign Application Priority Data

| Feb. 19, 2014 | (DE) | 10 2014 202 996 |
| Mar. 18, 2014 | (DE) | 10 2014 205 038 |
| Apr. 14, 2014 | (DE) | 10 2014 207 130 |

(51) Int. Cl.
*G02B 21/36* (2006.01)
*A61B 90/00* (2016.01)
(Continued)

(52) U.S. Cl.
CPC .............. *G02B 21/361* (2013.01); *A61B 3/13* (2013.01); *A61B 90/00* (2016.02);
(Continued)

(58) Field of Classification Search
CPC .. G02B 21/361; G02B 21/0012; A61B 90/00; A61B 3/13
(Continued)

(56) References Cited

U.S. PATENT DOCUMENTS

| 4,786,155 A | 11/1988 | Fantone et al. |
| 4,907,158 A | 3/1990 | Kettler et al. |

(Continued)

FOREIGN PATENT DOCUMENTS

| DE | 31 13 440 A1 | 11/1982 |
| DE | 101 57 613 A1 | 10/2002 |

(Continued)

OTHER PUBLICATIONS

International Search Report dated Aug. 12, 2015 of international application PCT/EP2015/053552 on which this application is based.

(Continued)

*Primary Examiner* — Jeffery A Williams
(74) *Attorney, Agent, or Firm* — Walter Ottesen, P.A.

(57) ABSTRACT

A surgical microscope for producing an observation image of an object region for an observer is provided. The surgical microscope includes an image acquisition device to acquire an image of the object region, a display device, an image processing and control device, a computer unit, a switchable imaging optical unit, an eyepiece and an optical observation beam path. The switchable imaging optical unit feeds the observation image to the eyepiece via the optical observation beam path in a first switching state. In a second switching state, the switchable imaging optical unit interrupts the optical observation beam path between the object region and the eyepiece to display an acquired image in the eyepiece and to electronically superpose the object region image data at a predefined position onto the image of the object region.

9 Claims, 14 Drawing Sheets

(51) Int. Cl.
*A61B 3/13* (2006.01)
*G02B 21/00* (2006.01)
*G02B 21/22* (2006.01)
*H04N 5/225* (2006.01)
*H04N 5/232* (2006.01)

(52) U.S. Cl.
CPC ......... *G02B 21/0012* (2013.01); *G02B 21/22* (2013.01); *G02B 21/365* (2013.01); *G02B 21/368* (2013.01); *H04N 5/2254* (2013.01); *H04N 5/23293* (2013.01); *A61B 2090/365* (2016.02)

(58) Field of Classification Search
USPC .......................................................... 348/80
See application file for complete search history.

(56) References Cited

U.S. PATENT DOCUMENTS

| | | | |
|---|---|---|---|
| 5,488,492 A | 1/1996 | Abe | |
| 5,657,128 A | 8/1997 | Mueller et al. | |
| 5,697,368 A | 12/1997 | Luber et al. | |
| 5,867,210 A | 2/1999 | Rod | |
| 5,867,309 A | 2/1999 | Spink et al. | |
| 6,483,948 B1* | 11/2002 | Spink | G02B 21/22 345/424 |
| 7,180,660 B2 | 2/2007 | Hauger et al. | |
| 7,688,503 B2 | 3/2010 | Hermann et al. | |
| 8,018,651 B2 | 9/2011 | Sander | |
| 8,115,993 B2 | 2/2012 | Hauger et al. | |
| 8,144,393 B2 | 3/2012 | Nakamura | |
| 8,427,743 B2 | 4/2013 | Sander | |
| 8,976,238 B2 | 3/2015 | Ernsperger et al. | |
| 2004/0061932 A1 | 4/2004 | Pensel et al. | |
| 2004/0165258 A1 | 8/2004 | Yamashita | |
| 2005/0063047 A1 | 3/2005 | Obrebski et al. | |
| 2007/0127115 A1 | 6/2007 | Hauger et al. | |
| 2008/0037113 A1 | 2/2008 | Nakamura | |
| 2008/0266656 A1* | 10/2008 | Sander | G02B 21/0012 359/372 |
| 2010/0259815 A1 | 10/2010 | Nakamura | |
| 2012/0056996 A1 | 3/2012 | Sander et al. | |

FOREIGN PATENT DOCUMENTS

| | | |
|---|---|---|
| DE | 10 2008 024 732 A1 | 1/2010 |
| DE | 10 2009 019 575 A1 | 11/2010 |
| DE | 10 2010 015 691 A1 | 10/2011 |
| DE | 10 2010 032 241 A1 | 1/2012 |
| DE | 10 2011 086 666 A1 | 5/2013 |
| JP | 10-133122 A | 5/1998 |

OTHER PUBLICATIONS

Translation of International Search Report dated Sep. 1, 2016 of international application PCT/EP2015/053552 on which this application is based.

* cited by examiner

SURGICAL MICROSCOPE FOR GENERATING AN OBSERVATION IMAGE OF AN OBJECT REGION

CROSS REFERENCE TO RELATED APPLICATIONS

This application is a continuation application of international patent application PCT/EP2015/053552, filed Feb. 19, 2015, designating the United States and claiming priority from German application Nos. 10 2014 202 996.1, filed Feb. 19, 2014, 10 2014 205 038.3, filed Mar. 18, 2014, and 10 2014 207 130.5, filed Apr. 14, 2014, and the entire content of the above applications is incorporated herein by reference.

FIELD OF THE INVENTION

The invention relates to a surgical microscope for generating an observation image of an object region for an observer including an image acquisition device for acquiring an image of the object region, a display device, and an image processing and control device which is connected to the image acquisition device and to the display device for the purpose of visualizing an image of the object region acquired by the image acquisition device.

The invention moreover relates to a method for producing an observation image of an object region for an observer, in particular by a surgical microscope, in which an image of the object region is acquired by an image acquisition device.

BACKGROUND OF THE INVENTION

Surgical microscopes are used in various medical disciplines, such as, for example, neurosurgery, minimally invasive surgery or else ophthalmology. They serve, in particular, to allow an operating medical practitioner to observe an operation region with magnification.

A surgical microscope of the type set forth at the outset is known from U.S. Pat. No. 4,786,155. In this surgical microscope, image data displayed on a display can be visualized for an observer in superposition with the image of the object region in an eyepiece. To this end, the surgical microscope has a beam splitter arranged in the optical observation beam path. This beam splitter mirrors an image of the object region displayed by a display into the optical observation beam path, the image being acquired by an image sensor in a characteristic wavelength range.

SUMMARY OF THE INVENTION

It is an object of the invention to provide a surgical microscope and to specify a method, which allow an observer to visualize an object region in a plurality of different ways in order to adapt the acquisition of images to the requirements of the observer, to the requirements of a patient and/or to different applications of a surgical microscope.

The object is achieved by providing a surgical microscope for producing an observation image of an object region for an observer, the surgical microscope including: an image acquisition device configured to acquire an image of the object region; a display device; an image processing and control device connected to said image acquisition device and to said display device to visualize the image of the object region acquired by said image acquisition device; a computer unit connected to said image processing and control device; said computer unit being configured to provide object region image data to said display device to be displayed on said display device; said object region image data being obtained by an imaging method; a switchable imaging optical unit having a first switching state and a second switching state; an eyepiece; an optical observation beam path being a purely optical observation part and being superposable with said object region image data at a predefined position; said switchable imaging optical unit being configured to feed the observation image of the object region to said eyepiece via said optical observation beam path being superposable with said object region image data at said predefined position when said switchable imaging optical unit is in said first switching state; said switchable imaging optical unit being configured to interrupt said optical observation beam path between the object region and said eyepiece in order to display an image from said optical observation beam path of the object region in said eyepiece that is acquired by said image acquisition device and displayed by said display device when said switchable imaging optical unit is in said second switching state; and, said image processing and control device being configured to electronically superpose the object region image data obtained by the imaging method and provided by the computer unit at the predefined position onto the image of the object region displayed by said display device in said eyepiece when said switchable imaging optical unit is in said second switching state.

The invention is based, firstly, on the discovery that visualizing an object region in an eyepiece by an optical observation beam path provides the advantage in a surgical microscope that a surgeon can observe an operating region with both very good optical imaging quality and a natural visual impression with color fidelity, even in the case of large magnification. Secondly, the invention is also based on the discovery that the digital acquisition and display of object structures in an operating region is advantageous in numerous applications of surgical microscopes. In fact, not only is comparatively little illumination light required for the digital acquisition and display of object structures in an operating region so that, in particular, radiation exposure of body tissue is thus reduced, but the digital acquisition and display of object structures in an operating region also render it possible to display to an observer tissue structures which cannot be acquired in the spectral range of the visible light.

Moreover, the invention is also based on the discovery that the visualization of data digitally acquired by an image acquisition device and subsequently prepared in a computer unit can make it easier for a surgeon to find his or her way around an operating region and it can also improve the manageability of a surgical microscope.

Therefore, the invention proposes the provision in a surgical microscope of a computer unit connected to the image processing and control device, for the provision of object region image data obtained by an imaging method, which are feedable to the display device as well as the provision of a switchable imaging optical unit which, in a first switching state, feeds the observation image of the object region to an eyepiece by an optical observation beam path, onto which the object region image data displayed by the display device are superposable at the correct position, and which, in a further switching state different from the first switching state, interrupts the optical observation beam path from the object region to the eyepiece in order to display an image of the object region from the optical observation beam path in the eyepiece, the image being acquired by the image acquisition device and displayed by the display device.

Here, object region image data obtained by an imaging method is understood to mean information in the form of images of the object region, which are preferably obtained prior to surgery, for example, by magnetic resonance imaging (MRI), positron emission tomography (PET), magnetoencephalography (MEG) or single photon emission computed tomography (SPECT). In particular, such object region image data can be angiography data, magnetic resonance imaging data, x-ray tomography data or spatially resolved image data acquired by an endoscope, laparoscope or microscope. In particular, object region image data obtained by an imaging method can be three-dimensional image data.

The surgical microscope according to an aspect of the invention includes a device for referencing a coordinate system stationary in relation to the surgical microscope to a coordinate system of the object region and to a coordinate system of object region image data obtained by an imaging method. Such a device for a surgical microscope is described in, for example, U.S. Pat. No. 5,657,128, which is referred to herewith and the disclosure of which is incorporated into the disclosure of this application.

This device renders it possible in the surgical microscope of the invention for the object region image data to be superposable, at the correct position, on the observation image of the object region in the surgical microscope by means of the display device.

For this superposition at the correct position, it is necessary for the coordinate system of the object region image data to be referenced or correlated with the coordinate system of the surgical microscope and with a coordinate system of the object region observed by the surgical microscope. This referencing or correlating of the coordinate systems is described, for example, in U.S. Pat. No. 5,697,368, which is referred to herewith and the disclosure of which is incorporated into the disclosure of this application. The correlating or referencing of the corresponding coordinate systems renders it possible to convert the coordinates of the object region image data in the coordinate system of the image data into the coordinate system of the surgical microscope in such a way that these image data are visualized for an observer with the image of the object region in such a way that mutually corresponding structures in the object region image data and in the image of the object region are superposed onto one another.

In particular, a surgical microscope according to an aspect of the invention can have a first eyepiece and a second eyepiece for stereoscopic visualization of a left-hand and right-hand partial image of the object region for an observer. Preferably, the switchable imaging optical unit is then used, in the first switching state, to feed the observation image of the object region to the second eyepiece with a further optical observation beam path and, in the further switching state different from the first switching state, to interrupt the further optical observation beam path from the object region to the second eyepiece. It is advantageous here if the image acquisition device then has a first image acquisition assembly and, additionally, a second image acquisition assembly for acquiring the left-hand and right-hand stereoscopic partial images of the object region. In particular, it is advantageous if, in the surgical microscope, the display device, connected to the image acquisition device, also serves to visualize the image of the object region, acquired by the image acquisition device, from the further optical observation beam path in the second eyepiece.

In fact, such a display device then also renders it possible, in particular, to visualize additional information for an observer, preferably in a picture-in-picture manner, such as, for example, angiography data, endoscopic images, x-ray recordings or magnetic resonance imaging images of a patient, which are superposable onto the image of the object region in the surgical microscope by electronic mixing in an image processing and control device.

Preferably, the switchable imaging optical unit also feeds the observation image of the object region to the second eyepiece with an optical observation beam path in the first switching state. By contrast, in the further switching state of the surgical microscope different from the first switching state, the optical observation beam path from the object region to the second eyepiece is interrupted in order to display an image of the object region from the further optical observation beam path in the second eyepiece, the image being acquired by the image acquisition device and displayed by the display of the display device.

In particular, it is a concept of the invention that the image processing and control device, in the further switching state, electronically superposes, at the correct position, object region image data provided by the computer unit and obtained in an imaging method onto the image of the object region displayed in the second eyepiece by the display device.

In particular, a surgical microscope according to the invention can also have a third eyepiece in order to produce an observation image of the object region for a co-observer. Here, it is advantageous to provide a display device, connected to the image acquisition device, with a display for visualizing the image of the object region, acquired by the first image acquisition device, in the third eyepiece. Then, the switchable imaging optical unit, in the first switching state, preferably feeds the observation image of the object region to the third eyepiece by a third optical observation beam path superposed onto the further optical observation beam path and, in the further switching state different from the first switching state, it interrupts the third optical observation beam path from the object region to the third eyepiece. What is achieved hereby is that an image of the object region from the optical observation beam path or from the further optical observation beam path can be displayed in the third eyepiece, the image being acquired by the first image acquisition device and displayed by the display of the display device.

Preferably, a surgical microscope according to an aspect of the invention also has a fourth eyepiece such that both a left-hand partial image and a right-hand partial image of the object region can thus be visualized for a co-observer.

Here, the switchable imaging optical unit, in the first switching state, feeds the observation image of the object region to the fourth eyepiece by a fourth optical observation beam path and, in the further switching state different from the first switching state, it interrupts the fourth optical observation beam path from the object region to the fourth eyepiece so that an image of the object region from the further optical observation beam path then is displayable in the fourth eyepiece, the image being acquired by the image acquisition device and displayed by the display of the display device.

Expediently, the image processing and control device in this case also electronically superposes, at the correct position, in the further switching state, object region image data, provided by the computer unit and obtained in an imaging method, onto the image of the object region displayed by the display device in the second eyepiece.

In particular, a surgical microscope according to an aspect of the invention can have a time-sequentially actuatable first shutter arranged in the third optical observation beam path and a time-sequentially actuatable further shutter arranged in the fourth observation beam path. Here, the first shutter and the further shutter are coupled to a display of the display device or of the further display device in such a way that a first partial image of the object region is visualized in the third eyepiece from the optical observation beam path by the display of the display device or of the further display device when the first shutter unblocks the third observation beam path and the further shutter interrupts the fourth observation beam path. Here, a second partial image of the object region is visualized in the fourth eyepiece from the further optical observation beam path by the display of the display device or of the further display device when the first shutter interrupts the third observation beam path and the further shutter unblocks the fourth observation beam path.

According to another aspect of the invention, a device for separating pupils is provided in such a surgical microscope, the device dividing a beam path, decoupled from a purely optical observation beam path, into a first stereoscopic partial beam path, feedable to the third eyepiece as third optical observation beam path, and into a second stereoscopic partial beam path, feedable to the fourth eyepiece as fourth optical observation beam path.

According to another aspect of the invention, an image acquisition device is provided, in an eyepiece, for acquiring a first stereoscopic partial image, decoupled from a purely optical observation beam path to the eyepiece, and for acquiring a second stereoscopic partial image, decoupled from the purely optical observation beam path to the eyepiece, of the object region in a surgical microscope for producing an observation image of an object region for an observer. Here, the image acquisition device is connected to a display device for the stereoscopic visualization of the first stereoscopic image of the object region and of the second stereoscopic partial image of the object region.

In accordance with yet another aspect of the invention, provision is made for the display device to be able to provide a first stereoscopic partial image of the object region in a first eyepiece and a second stereoscopic partial image of the object region in a second eyepiece. Here, the first eyepiece and the second eyepiece are preferably movably arrangeable as desired in the three spatial directions in view of the imaging optical unit.

Here, it is advantageous to provide a position sensor for evaluating the azimuthal position of the first eyepiece and the second eyepiece, wherein the image acquisition device then is connected to an image processing and control device, which feeds the first stereoscopic partial image or the second stereoscopic partial image of the object region to the display device in a rotational position dependent on the evaluated azimuthal position in order to visualize the object region in the first eyepiece and in the second eyepiece with an image display corresponding to different directions of view.

In particular, a surgical microscope according to an aspect of the invention can have a visualization device, connected to the image acquisition device, for visualizing images of the object region. By way of example, this visualization apparatus can also contain a screen. Preferably, a surgical microscope according to an aspect of the invention includes a visualization device, connected to the first image acquisition device and to the second image acquisition device, for the stereoscopic visualization of images of the object region. To this end, this visualization device can include, for example, a 3D screen.

It should be noted that a surgical microscope according to an aspect of the invention can also have a plurality of binocular tubes for the main observation and a plurality of binocular tubes for the co-observation with appropriate eyepieces, in which the image of the object region is displayed to an observer selectively by an optical observation beam path or by a display device with a display.

In the method according to an aspect of the invention, an image of the object region is acquired with an image acquisition device for generating an observation image of an object region for an observer. Here, the image of the object region is displayed to the observer selectively by a purely optical observation beam path or by a display device, to which the image, of the object region, acquired by the image acquisition device is fed. Here, the object region image data obtained in an imaging method are preferably superposed in each case, at the correct position, onto the image of the object region.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
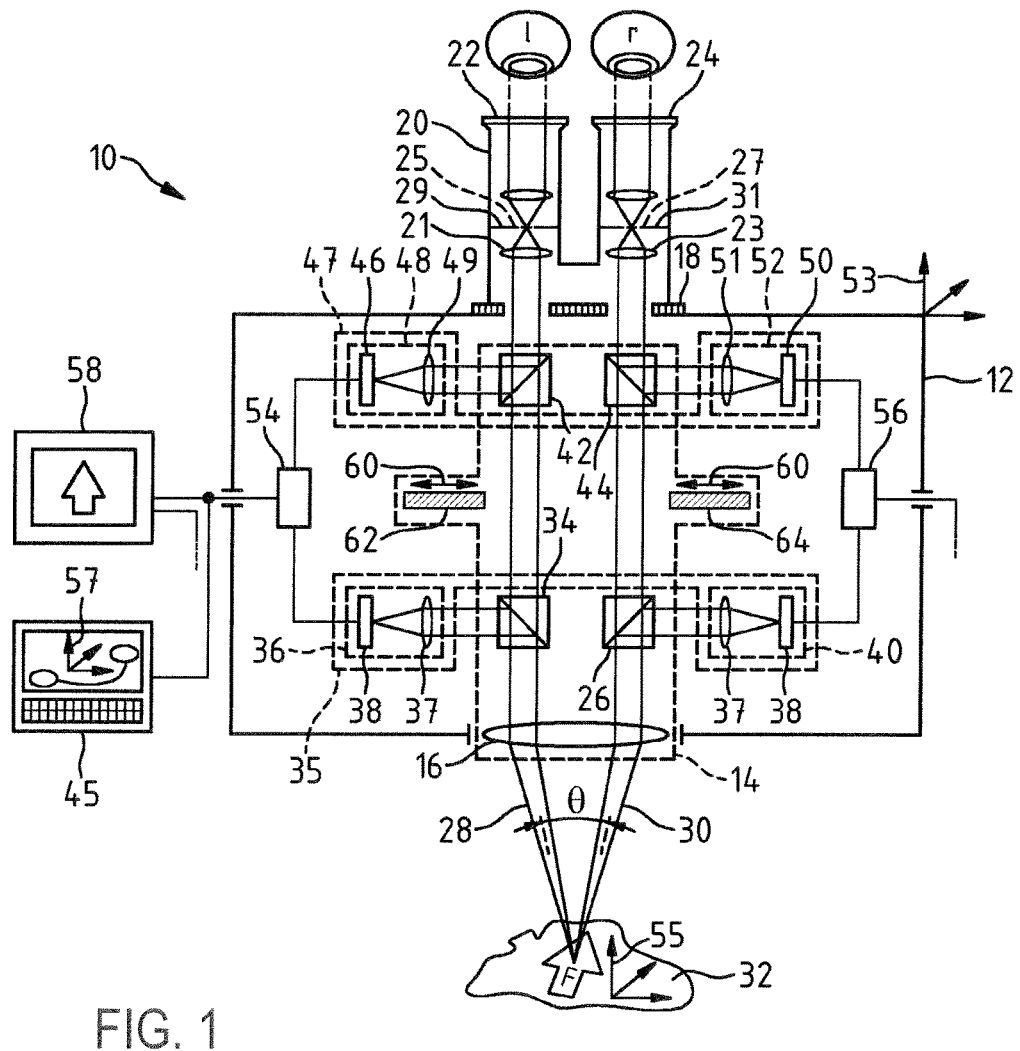
FIG. 1 shows a first surgical microscope including a binocular tube for the stereoscopic visualization of an object region in a first operating state.

The first stereoscopic surgical microscope 10, shown in FIG. 1, has a surgical microscope main body 12, in which a switchable imaging optical unit 14 with a microscope main objective system 16 is accommodated. It has a binocular tube 20 connected to the main body 12 at an interface 18, including a first eyepiece 22 and a second eyepiece 24 for a left and a right eye 72 and 74 of an observer. A first observation beam path 28 and a second observation beam path 30 from an object region 32 passes through the microscope main objective system 16 in the surgical microscope 10.

The imaging optical unit 14 includes an output coupling beam splitter 34 arranged in the first optical observation beam path 28 on the side of the microscope main objective system 16 distant from the object region 32, the output coupling beam splitter decoupling some of the observation light from the first observation beam path 28 and feeding it to an image acquisition device 35. The image acquisition device 35 includes a first image acquisition assembly 36 having an objective lens system 37 and an image sensor 38, and a second image acquisition assembly 40 including an objective lens system 37 and an image sensor 38.

Moreover, the imaging optical unit 14 has a further output coupling beam splitter 26 arranged in the second optical observation beam path 30 on the side of the microscope main objective system 16 distant from the object region 32, the further output coupling beam splitter decoupling some of the observation light from the second observation beam path 30 and guiding it to the image acquisition device 35 including the objective lens system 37 and the image sensor 38 of the image acquisition device 35.

There is an input coupling beam splitter 42 and an input coupling beam splitter 44 in the imaging optical unit 14. By way of the input coupling beam splitters 42 and 44, it is possible to superpose display information, displayed on a display 46 of a display assembly 48 of a display device 47 and on a display 50 of a display assembly 52 of the display device 47, onto the image of the object region 32 in the first optical observation beam path 28 and in the second optical observation beam path 30. To this end, the displays 46 and 50 of display assemblies 48 and 52 of the display device 47 are preferably embodied as a "digital mirror display" (DMD), which enables quick interchange between images displayed therewith.

By the input coupling beam splitters 42 and 44, it is possible to superpose display information in particular, for example, in the form of three-dimensional angiography data obtained prior to surgery, onto the image of the object region 32, which is fed to the eyepiece 22 and the eyepiece 24 of the binocular tube 20.

To this end, the display information 46 and 50 of the display assemblies 48 and 52 is transferred into a parallel beam path by a display lens 49 and 51 in each case and imaged into the left-hand intermediate image plane 25 and right-hand intermediate image plane 27 of the binocular tube 20 by the tube lenses 21 and 23. The intermediate image in the left-hand and right-hand intermediate image plane 25 and 27 is restricted by an ocular field stop 29 and 31 in the binocular tube 20. The imaging scale of the images of the displays 46 and 50 in the left-hand intermediate image plane 25 and right-hand intermediate image plane 27 is determined here by the ratio $f_D/f_T$ of the focal length $f_D$ of the display lenses 49 and 51 and the focal length $f_T$ of the tube lenses 21 and 23.

For the purposes of actuating the displays 46 and 50, the surgical microscope 10 includes an image processing and control device 54 and an image processing and control device 56, which is connected to a computer unit 45. It should be noted that the computer unit 45 can be arranged externally, in particular, in relation to the main body of the surgical microscope 10. The computer unit 45 serves for the provision of spatially resolved three-dimensional object region image data, which are fed to the display device 47 for the display, and which are obtained, for example, prior to surgery in an imaging method, for example, by magnetic resonance imaging or x-ray tomography.

Here, the computer unit 45 provides the three-dimensional object region image data as image data referenced to the coordinate system of the object region 32 and the coordinate system of surgical microscope 10. To this end, the computer unit 45 includes a computer program which references a coordinate system 53 stationary in relation to the surgical microscope 10 to a coordinate system 55 stationary in relation to the object region 32 and to a coordinate system 57 of the object region image data from position information about the surgical microscope 10 and position information about the object region 32.

In order to visualize the images of the object region 32 acquired from the first optical observation beam path 28 and the second optical observation beam path 30 by the image acquisition device 35, the surgical microscope 10 has an image reproduction device 58, preferably embodied as a 3D monitor, which is connected to the image processing and control device 56.

The imaging optical unit 14 of the surgical microscope 10 includes a shutter element 62 and a shutter element 64. The shutter elements 62 and 64 can be displaced by a drive (not shown here) in accordance with the double-headed arrow 60. With the shutter elements 62 and 64, it is possible to selectively unblock or block the first optical observation beam path 28 and/or the second optical observation beam path 30 on the side of the output coupling beam splitter 34 and 26 distant from the microscope main objective system 16.

In the operating state of the surgical microscope shown in FIG. 1, the imaging optical unit 14 is switched in such a way that the shutter element 62 and the shutter element 64 unblock the first optical observation beam path 28 and the second optical observation beam path 30. Then, the purely optical observation beam path 28 or 30 from the object region 32, passing through the microscope main objective system 16, is fed to the first eyepiece 22 and the second eyepiece 24 of the binocular tube 20 in the surgical microscope 10. Here, object region image data displayed by the display device 47 are superposed, at the correct position, onto the observation image of the object region 32 in the first eyepiece 22 and in the second eyepiece 24.

Figure 2:
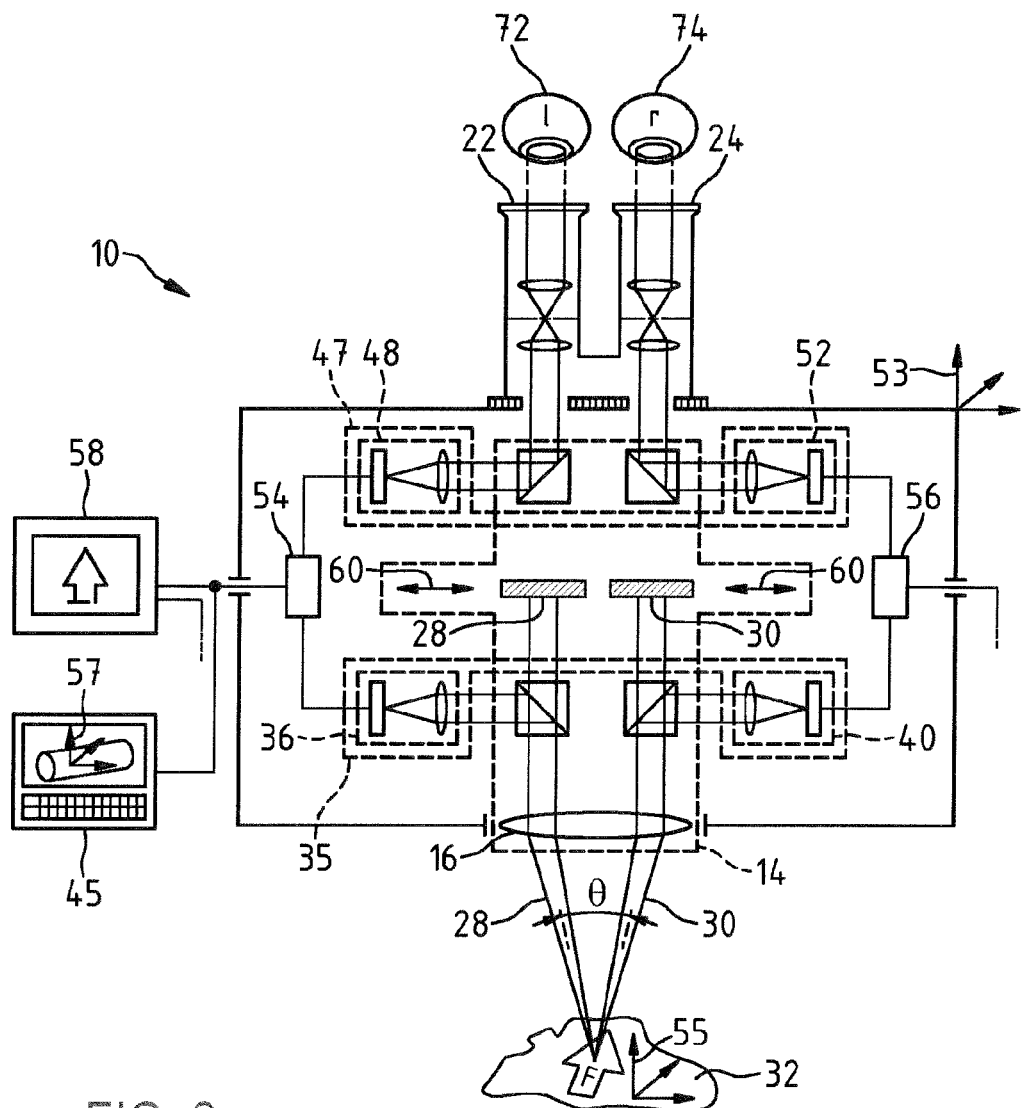
FIG. 2 shows the first surgical microscope in a second operating state.

FIG. 2 shows the surgical microscope 10 in a further operating state, in which the shutter element 62 and the shutter element 64 block the first optical observation beam path 28 and the second optical observation beam path 30. Here, the image of the object region 32 acquired by the image acquisition assemblies 36 and 40 of the image acquisition device 35 and displayed by the display assemblies 48 and 52 is fed in each case to the first eyepiece 22 and the second eyepiece 24 of the binocular tube 20 in the surgical microscope 10.

Hence, a left-hand stereoscopic partial image of the object region 32 can be fed to the image acquisition assembly 36 of the image acquisition device 35 by the first optical observation beam path 28 and a right-hand stereoscopic partial image of the object region 32 can be fed to the image acquisition assembly 40 of the image acquisition device 35 by the second optical observation beam path 30. Here, the optical axes of the first optical observation beam path 28 and of the second optical observation beam path 30 include a stereo angle θ. This renders it possible to also visualize the object region 32 stereoscopically by the surgical microscope 10 when the first optical observation beam path 28 and the second optical observation beam path 30 are blocked by the shutter elements 62 and 64. To this end, the left-hand stereoscopic partial image in the binocular tube 20 then is produced by the display assembly 48 and the right-hand stereoscopic partial image is produced by the display assembly 52 of the display device 47.

It should be noted that it is possible in the surgical microscope 10 to display not only the image of the object region 32 with the display assemblies 48 and 52 but also further information as well, in particular image information in object region image data, such as, for example, angiography data, endoscopic images, x-ray recordings or else magnetic resonance imaging images of a patient, which are combined in the image processing and control devices 54 and 56 by electronic mixing with the image of the object region 32 acquired by the image acquisition device 35. Here, the object region image data provided by the computer unit 45 are electronically superposed, at the correct position, onto the image, of the object region, displayed in the eyepiece 22 by the display device 47.

Figure 3A:
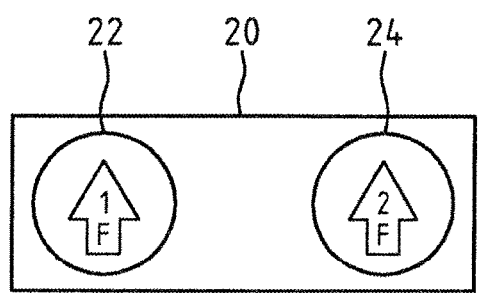
FIG. 3A and FIG. 3B show a binocular vision in the binocular tube of the surgical microscope in the first operating state and in the second operating state.

FIG. 3A shows a left-hand stereoscopic partial image 1 produced by the optical observation beam path 28 and a right-hand stereoscopic partial image 2 produced by the optical observation beam path 30, this being perceived by an observer as the image of the object region 32 when looking into the first eyepiece 22 and second eyepiece 24 of the binocular tube 20.

Figure 3B:
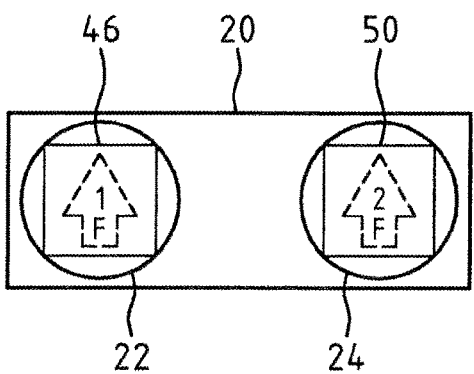

In FIG. 3B, the left-hand stereoscopic partial image 1 displayed by the display assembly 48 and the right-hand stereoscopic partial image 2 displayed by the display assembly 52 are shown in the first eyepiece 22 and second eyepiece 24 of the binocular tube 20, this being perceived by an observer in the binocular tube 20 as the image of the object region 32 in the operating state of the surgical microscope 10 shown in FIG. 2.

Figure 4:
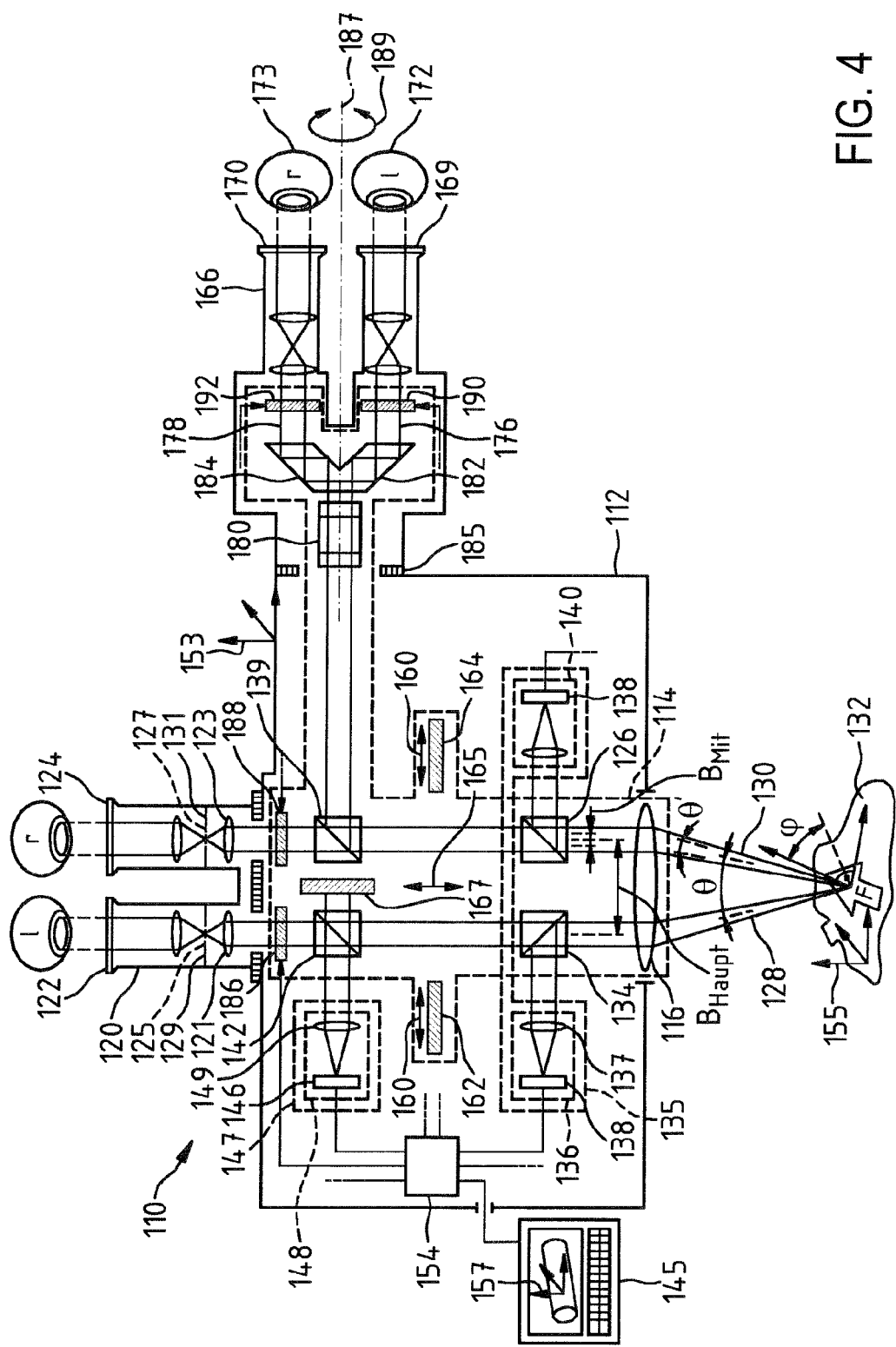
FIG. 4 shows a second surgical microscope including a binocular tube for main observation and a binocular tube for co-observation for stereoscopic visualization of the object region in a first operating state.
Figure 5:
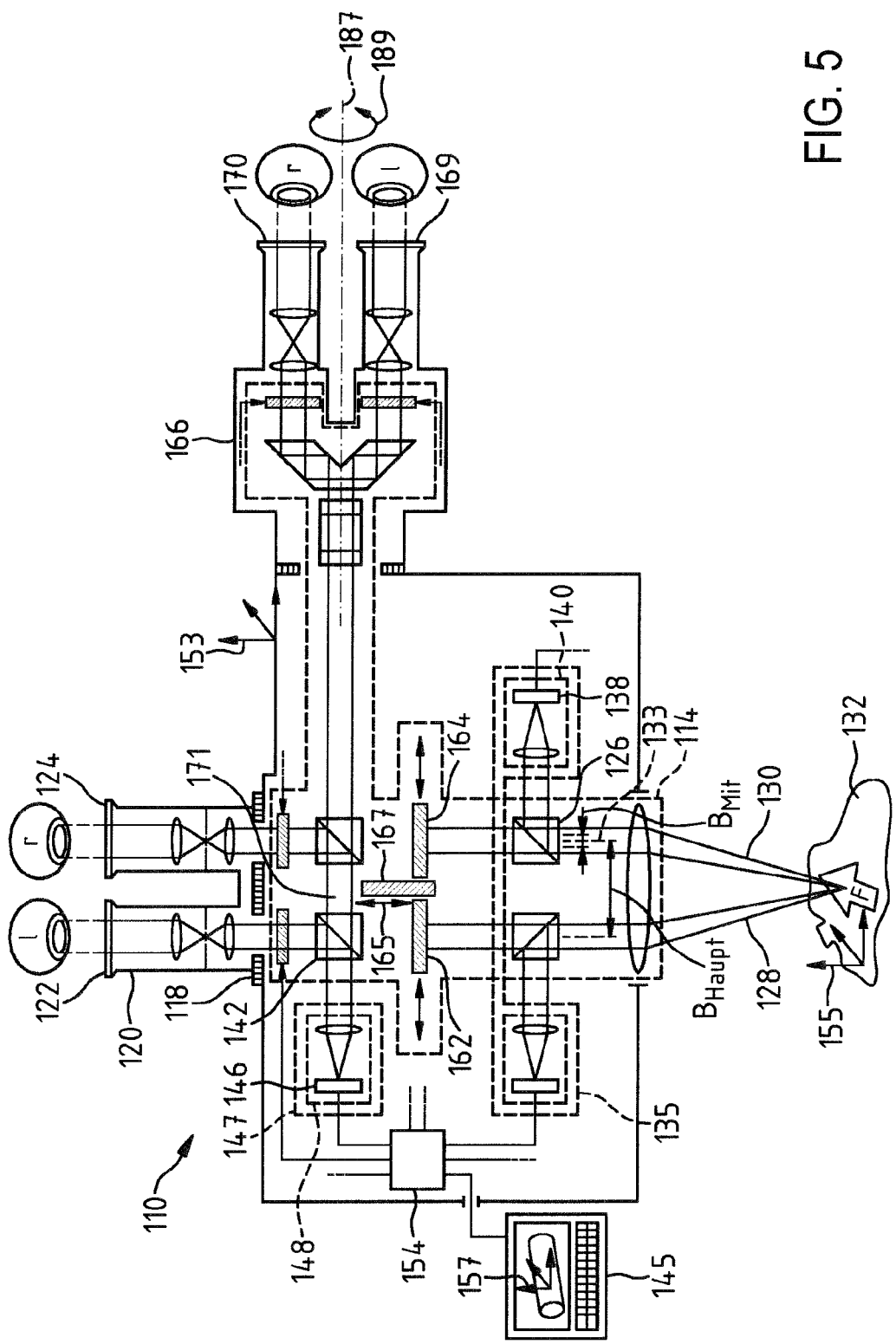
FIG. 5 shows the second surgical microscope in a second operating state.

FIG. 4 shows a second stereoscopic surgical microscope 110 in a first operating state. In FIG. 5, the second surgical microscope 110 is shown in a further operating state different from the first operating state.

The surgical microscope 110 has a binocular tube 120 for the main observation and has a further binocular tube 166 for co-observation. To the extent that elements and the assemblies and beam paths in the surgical microscope 110 in FIG. 4 and FIG. 5 functionally correspond to the assemblies and beam paths in the surgical microscope 10 described in FIGS. 1 and 2 and to the elements shown in these figures, these are denoted in FIG. 4 by numbers as reference signs which have been increased by the number 100 in relation to FIG. 1.

The surgical microscope 110 has a surgical microscope main body 112 which accommodates a switchable imaging optical unit 114 with a microscope main objective system 116.

The binocular tube 166 has an eyepiece 169 and an eyepiece 170 for the left eye 172 and the right eye 174 of a further observer. A third and a fourth eyepiece are provided in the surgical microscope 110 by the eyepieces 169, 170.

For the sake of clarity, the binocular tube 166 with the Dove prism 180 is shown in a position in which the latter is rotated by an angle of 90° about the axis 187 from a horizontal plane perpendicular to the sectional plane of the surgical microscope main body 112.

In the surgical microscope 110, a first observation beam path 128 and a second observation beam path 130 as well as a third observation beam path 176 and a fourth observation beam path 178 pass through the microscope main objective system 116. Here, the third observation beam path 176 and the fourth observation beam path 178 are partly guided in the second observation beam path 130. Here, the binocular tube 166 enables the stereoscopic observation of the object region 132 for an observer with the stereo angle θ'<θ.

The imaging optical unit 114 includes an output coupling beam splitter 134 arranged in the first optical observation beam path 128 on the side of the microscope main objective system 116 distant from the object region 132, the output coupling beam splitter deflecting some of the observation light from the first observation beam path 128 and guiding it to an image acquisition device 135, which contains a first image acquisition assembly 136 with an objective lens system 137 and an image sensor 138 and a second image acquisition assembly 140 with an objective lens system 137 and the image sensor 138.

In the surgical microscope 110, the third observation beam path 176 and the fourth observation beam path 178 are fed to the eyepiece 169 and the eyepiece 170 of the binocular tube 166 via an output coupling beam splitter 139 arranged in the second observation beam path 128 and a Dove prism 180 rotatably mounted in the binocular tube 166, through a pupil separation mirror system 182 and 184.

The binocular tube 166 is connected to an interface 185 of the surgical microscope main body 112, like the binocular tube 120. Here, the binocular tube 166 can be rotated about an axis 187 passing through the surgical microscope main body 112 in accordance with the double-headed arrow 189.

In the housing of the binocular tube 166, the Dove prism 180 can be freely rotated about the axis 187 relative to the binocular tube 166 and the surgical microscope main body 112. Here, the rotation of the Dove prism 180 brings about a displacement of the azimuthal position of the stereo basis BCo, denoted by the angle φ in the object region 132, of the perspective visual impression in the binocular tube 166 in relation to the optical axis of the observation beam path 130.

The imaging optical unit 114 of the surgical microscope 110 includes respectively one time-sequentially actuatable shutter 186, 188, 190, and 192 in the first optical observation beam path 128, in the second optical observation beam path 130, in the third optical observation beam path 176 and in the fourth optical observation beam path 178. The shutters 186, 188, 190 and 192 are arranged in the respective observation beam path 128, 130, 176, and 178 on a side of the input coupling beam splitter 142 and the output coupling beam splitter 139 distant from the microscope main objective system 116 and they can selectively unblock or interrupt the relevant observation beam path by way of a suitable actuation. Here, the shutters 186, 188, 190 and 192 are configured for operation with a switching frequency of, for example, 100 Hz or else higher switching frequencies.

The surgical microscope 110 also has an image processing and control device 154 which, in this case, feeds the image of the object region 132, acquired by the image acquisition assemblies 136 and 140, in the first optical observation beam path 128 and the second optical observation beam path 130 to the display device 147.

The imaging optical unit 114 in the surgical microscope 110 in each case includes a shutter element 162 and 164 arranged in the first optical observation beam path 128 and in the second optical observation beam path 130, and displaceable in accordance with the double-headed arrow 160. Moreover, the imaging optical unit 114 in the surgical microscope 110 has an additional shutter element 167 which is displaceable in accordance with the double-headed arrow 165. By the shutter element 167, an optical beam path 171 passing through the input coupling beam splitter 142 can be unblocked and blocked between the input coupling beam splitter 142 and the output coupling beam splitter 139.

In this manner, it is selectively possible not only to provide the display information displayable by the display device 147 in the first optical observation beam path 128 by way of the input coupling beam splitter 142 but also, additionally, to display the display information in the third eyepiece 169 and fourth eyepiece 170 of the binocular tube 166 by a beam path passing through the output coupling beam splitter 139.

The image processing and control device 154 in the surgical microscope 110 is connected to the time-sequentially actuatable shutters 186, 188, 190, and 192. In the operating state of the surgical microscope 110 shown in FIG. 4, the time-sequentially actuatable shutters 186, 188, 190, and 192 unblock the first optical observation beam path 128, the second optical observation beam path 130, the third optical observation beam path 176 and the fourth optical observation beam path 178.

When the shutter element 167 unblocks the optical beam path 171 between the input coupling beam splitter 142 and the output coupling beam splitter 139, the surgical microscope 110 enables the display of display data, superposed onto the optical observation beam path 128, 130, 176 and 178 by the beam splitters (142, 139), in the first eyepiece 122 and the further eyepiece 124 of the binocular tube 120 and in the two eyepieces (169, 170) of the binocular tube 166.

It should be noted that, in the setting shown in FIG. 4, the surgical microscope 110 can, in principle, also be operated with a switched-off display.

FIG. 5 shows the surgical microscope 110 in an operating state in which the shutter element 162 and the shutter element 164 block the first optical observation beam path 128 and the second optical observation beam path 130 and in which the shutter element 167 unblocks the beam path 171 between the input coupling beam splitter 142 and the output coupling beam splitter 139. Here, an image of the object region 132, which is acquired by the image acquisition devices 136 and 138 and displayed by the display device 148, is respectively shown in the first eyepiece 122 and second eyepiece 124 of the binocular tube 120 and in the third eyepiece 169 and fourth eyepiece 170 of the binocular tube 166 of the surgical microscope 110 by virtue of the shutters 186, 188, 190, and 192 being actuated in a manner tuned to the display area of the display 146. However, unlike the setting of the surgical microscope 110 shown in FIG. 4, an adjustment of the Dove prism does not in this case bring about an azimuthal displacement of the stereo basis $B_{Main}$ for the stereoscopic visual impression then perceivable in the binocular tube 166.

Figure 6A:
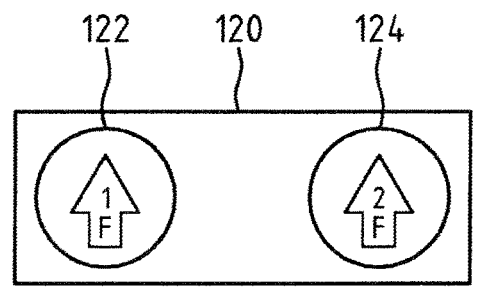
FIG. 6A and FIG. 6B show a binocular vision in the binocular tube for the main observation and in the binocular tube for the co-observation of the second surgical microscope in the first operating state and in the second operating state.
Figure 6A:
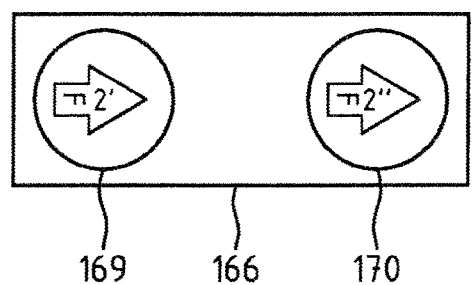

FIG. 6A shows a left-hand stereoscopic partial image 1 produced by the optical observation beam path 128 and a right-hand stereoscopic partial image 2 produced by the optical observation beam path 130, this being perceived by an observer when looking into the first eyepiece 122 and second eyepiece 124 of the binocular tube 120 of a main observer.

The left-hand stereoscopic partial image 2' produced by the optical observation beam path 176 and the right-hand stereoscopic partial image 2" produced by the optical observation beam path 178 in the third eyepiece 169 and in the fourth eyepiece 170 of the binocular tube 166 in the surgical microscope 110 are perceived in this case as an image of the object region 132 by a co-observer, this having a perspective which, in principle, corresponds to the perspective perceived by a main observer in the binocular tube 120. However, the co-observer stereo basis $B_{Co}$ underlying the perspective visual impression in the binocular tube 166 in this case is smaller than the stereo basis $B_{Main}$ of the perspective visual impression in the binocular tube 120.

When moving the binocular tube 166 in accordance with the double-headed arrow 189 and/or when rotating the Dove prism 180 about the axis 187, the stereo basis $B_{Co}$ of the perspective visual impression in the binocular tube 166 is rotated about the optical axis 133 of the observation beam path 130.

Figure 6B:
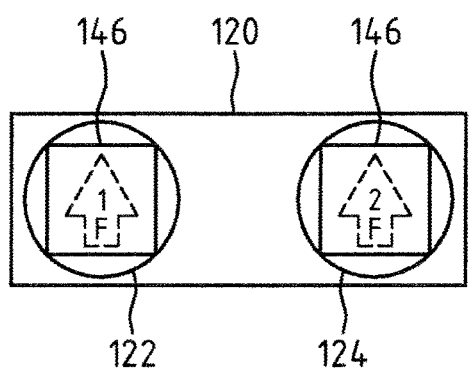
Figure 6B:
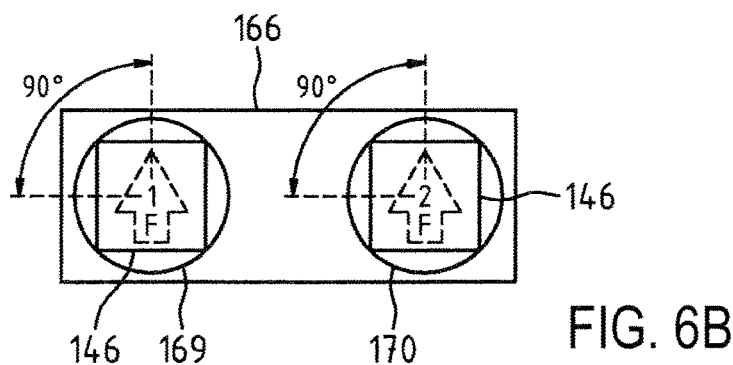

In FIG. 6B, the left-hand stereoscopic partial image 1 as displayed by the display device 147 and the right-hand stereoscopic partial image 2 in the first eyepiece 122 and second eyepiece 124 of the binocular tube 120, and in the third eyepiece 169 and the fourth eyepiece 170 of the binocular tube 166, can be seen as they are perceived by an observer in the binocular tube 120 and in the binocular tube 166 as the image of the object region 132 in the operating state of the surgical microscope 110 shown in FIG. 5.

The partial images 1, 2 shown in FIG. 6B can be displayed to an observer in the binocular tube 120 and in the binocular tube 166 as the image of the object region 132 when the image processing and control device 154 displays the image of the object region 132, acquired by the image acquisition device 135, on the display 146 of the display device 147 and by virtue of in this case, firstly, the shutters 186 and 190 and, secondly, the shutters 188 and 192 being switched synchronously with the display device 147 to be alternatively transparent and opaque for light in the respective beam path for the purposes of displaying the image of the object region 132 acquired by the image acquisition device 135.

In this case, the co-observer stereo basis $B_{Co}$ underlying the perspective vision in the binocular tube 166 and the stereo basis $B_{Main}$ for the perspective vision in the binocular tube 120 are of the same size. However, in this case, the same stereoscopic image of the object region 132 is shown to a co-observer in the binocular tube 166 and to a main observer in the binocular tube 120, even though the viewing position of the binocular tube 166 is rotated through an angle of 90° about the optical axis of the microscope main objective 116 of the surgical microscope 110 in relation to the viewing position of the binocular tube 120.

In this context, it should be noted that, in the setting of the surgical microscope 110 shown in FIG. 5, the left-hand and right-hand partial images 1 and 2 shown in FIG. 6B are rotated in the binocular eyepieces 169 and 170 of the binocular tube, as indicated by the double-headed arrows in FIG. 6B, in the case of a movement of the binocular tube 166 or of the Dove prism 180 about the axis 187.

Figure 7:
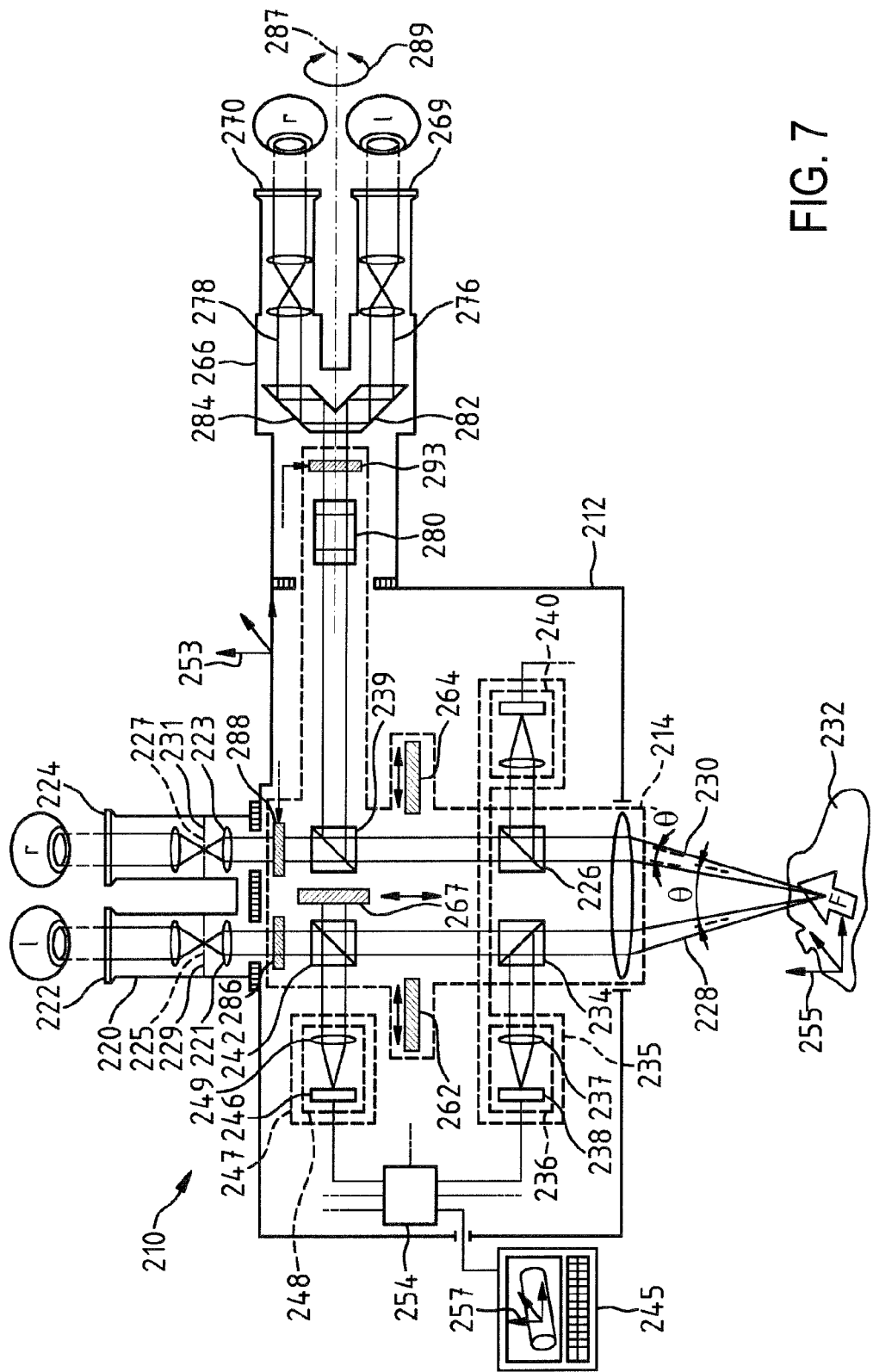
FIG. 7 shows a third surgical microscope for stereoscopic visualization of the object region in a first operating state including a binocular tube for the main observation and a binocular tube for the co-observation.
Figure 8:
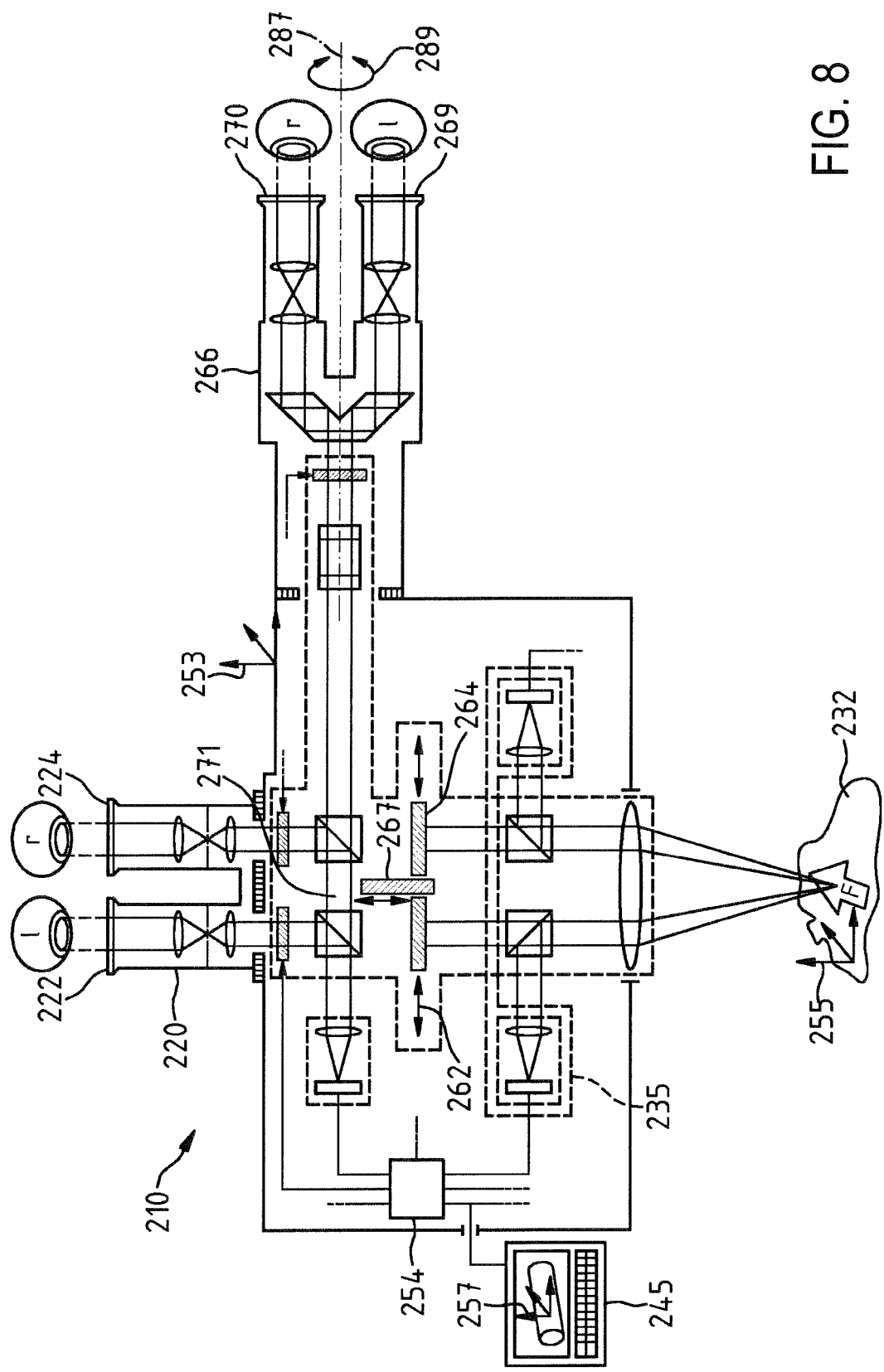
FIG. 8 shows the third surgical microscope in a second operating state.

FIG. 7 shows the third stereoscopic surgical microscope 210 in a first operating state. In FIG. 8, the third surgical microscope 210 is shown in a second operating state. The surgical microscope 210 has a binocular tube 220 for the main observation and it has a further binocular tube 266 for the co-observation. To the extent that elements and assemblies and beam paths in the surgical microscope 210 in FIG. 7 and FIG. 8 functionally correspond to the assemblies and beam paths in the surgical microscope 110 described on the basis of FIGS. 4 and 5 and to the elements shown in these figures, these are denoted in FIG. 7 and FIG. 8 by numbers as reference signs which have been increased by the number 100 in relation to FIG. 4.

Unlike the surgical microscope 110, the surgical microscope 210 includes a time-sequentially actuatable shutter 293 arranged between the Dove prism 280 and the pupil separation mirror system 282 and 284 in the binocular tube 266.

Figure 9A:
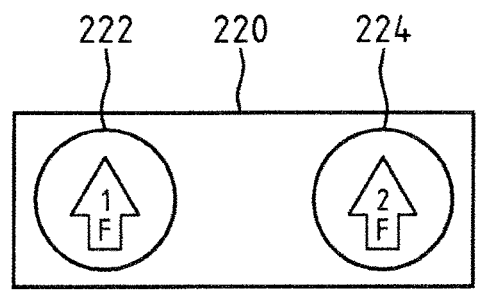
FIG. 9A and FIG. 9B show the binocular vision in the binocular tube for the main observation and the binocular tube for the co-observation of the third surgical microscope in the first operating state and in the second operating state.
Figure 9A:
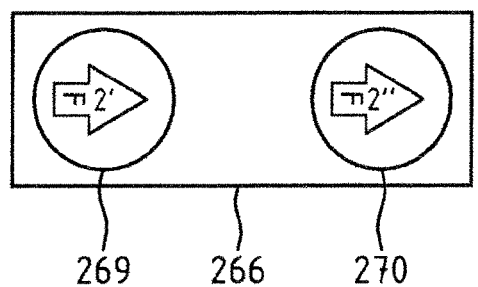

FIG. 9A shows a left-hand stereoscopic partial image 1 produced by the optical observation beam path 228 and a right-hand stereoscopic partial image 2 produced by the optical observation beam path 230, this being perceived by an observer in the first operating state of the surgical microscope 210 shown in FIG. 7 when looking into the first eyepiece 222 and second eyepiece 224 of the binocular tube 220 of a main observer.

The left-hand stereoscopic partial image 2' produced by an optical observation beam path 276 and the right-hand stereoscopic partial image 2" produced therein by an optical observation beam path 278 in the third eyepiece 269 and in the fourth eyepiece 270 of the binocular tube 266 in the surgical microscope 210 is perceived in this case by a co-observer as a stereoscopic image of the object region 232. However, the co-observer stereo basis $B_{Co}$ underlying the perspective vision in the binocular tube 266 is likewise smaller in this case than the stereo basis $B_{Main}$ for the perspective vision in the binocular tube 220.

When moving the binocular tube 266 about the axis 287, the stereo basis $B_{Co}$ of the perspective visual impression in the binocular tube 266 is rotated about the optical axis of the observation beam path 230.

Figure 9B:
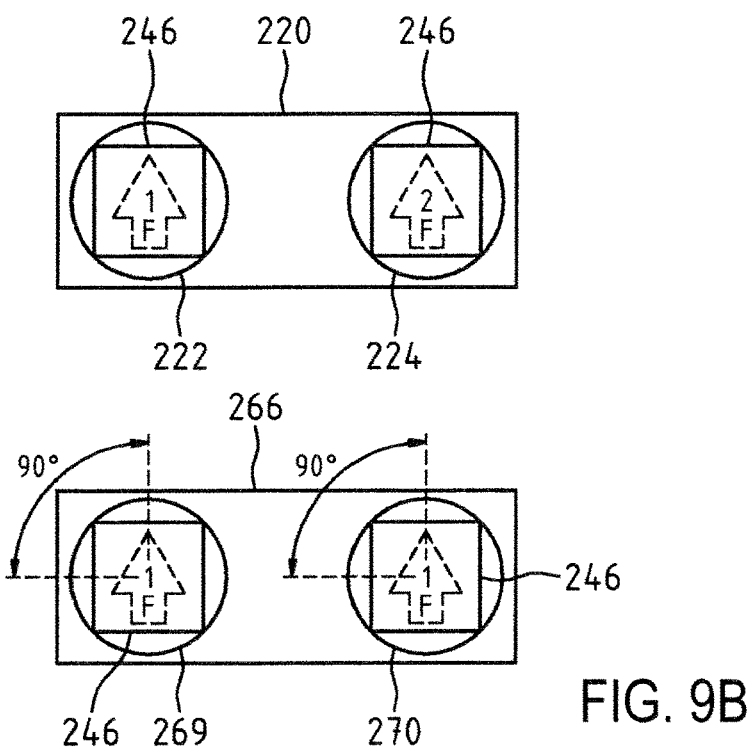

FIG. 9B shows the left-hand stereoscopic partial image 1 and right-hand stereoscopic partial image 2 in the first eyepiece 222 and second eyepiece 224 of the binocular tube 220 and in the third eyepiece 269 and fourth eyepiece 270 of the binocular tube 266, displayed by the display device 247, in the operating state of the surgical microscope 210 shown in FIG. 8. The partial images 1 and 2 can be displayed by an observer in the binocular tube 220 and in the binocular tube 266 as the image of the object region 232 by virtue of the image processing and control device 254 displaying on the display 246 of the display device 247 the image of the object region 232 acquired by the image acquisition assembly 236 and 240 and by virtue of in this case, firstly, the shutters 286 and 293 and, secondly, the shutter 288 being switched synchronously to be alternatively transparent and opaque for light in the respective beam path for the purposes of displaying the image of the object region 232 acquired by the image acquisition assembly 236 and 240.

Unlike the visual impression for a main observer in the binocular tube 220, the visual impression for a co-observer in the binocular tube 266 is not perspective in this case.

If the binocular tube is rotated in this case about the axis 287 in accordance with the double-headed arrow 289 from FIG. 5, the same left-hand and right-hand partial images, indicated by dashed lines, are displayed to the co-observer. When moving the binocular tube 266 or the Dove prism 280 about the axis 287, these partial images in the binocular eyepieces 269 and 270 of the binocular tube are rotated, as indicated in FIG. 9B by the double-headed arrows.

Figure 10:
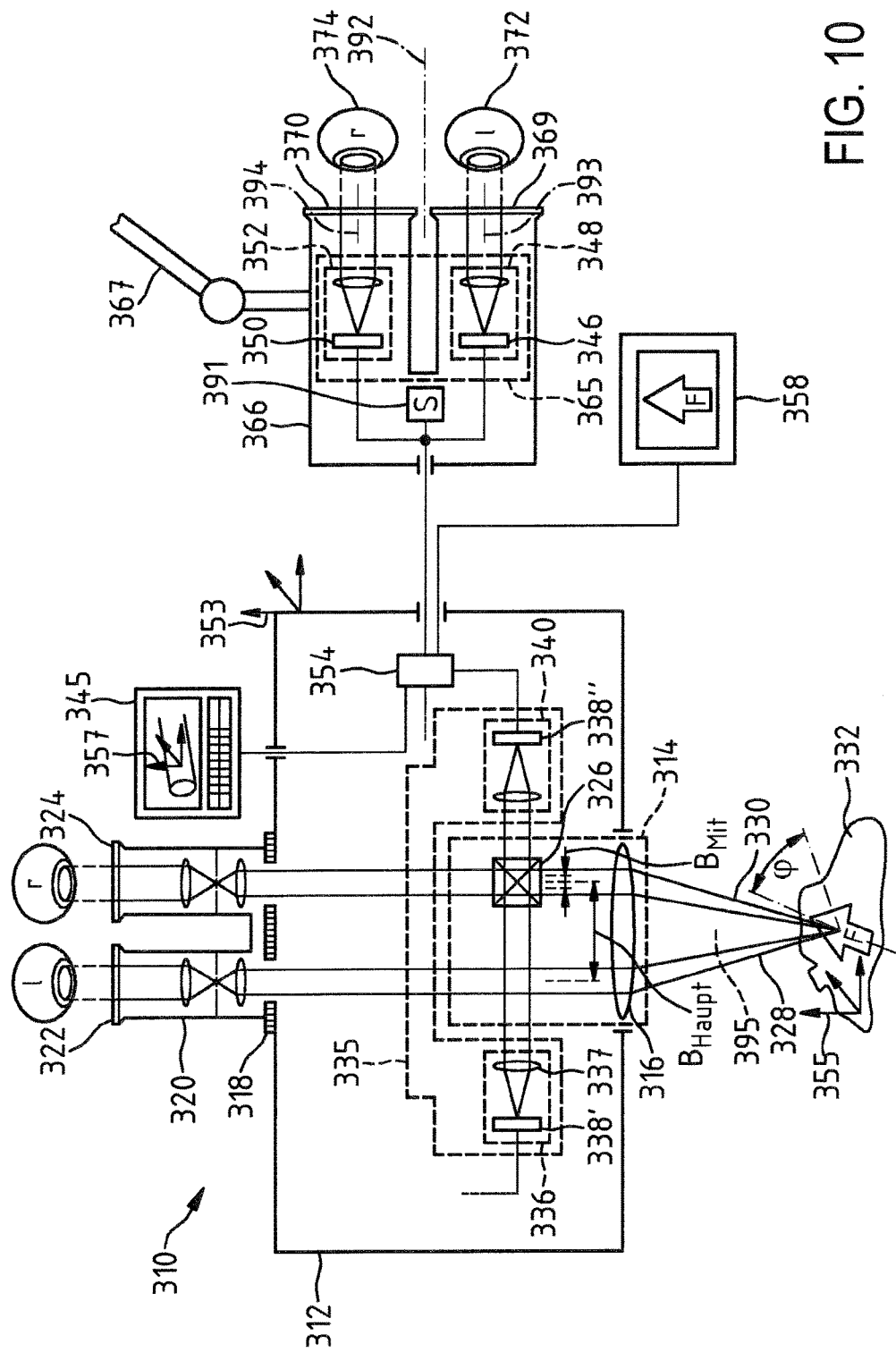
FIG. 10 shows a fourth surgical microscope for stereoscopic visualization of the object region including a binocular tube for the main observation and a binocular tube for the co-observation.

The fourth stereoscopic surgical microscope 310, shown in FIG. 10, has a surgical microscope main body 312 which accommodates a switchable imaging optical unit 314 with a microscope main objective system 316 and it likewise includes a binocular tube 320, connected to the main body at an interface 318, for the main observation with a first eyepiece 322 and a second eyepiece 324. Moreover, the surgical microscope 310 has a further binocular tube 366 for the co-observation. For an observer, the binocular tube 366 acts as a display device with a display 346 and 350. In the surgical microscope 310, it provides an additional third eyepiece 369 and fourth eyepiece 370 for the left eye 372 and right eye 374 of a further observer. The binocular tube 366 is accommodated in a holding system 367 and it can therefore be displaced relative to the binocular tube 320 and relative to the surgical microscope main body 312.

To the extent that elements and assemblies and beam paths in the surgical microscope 310 shown in FIG. 10 functionally correspond to the assemblies and beam paths in the surgical microscope 110 described on the basis of FIGS. 4 and 5 and to the elements shown in these figures, these are denoted in FIG. 10 by numbers as reference signs which have been increased by the number 200 in relation to FIG. 4.

The imaging optical unit 314 in the surgical microscope 310 has a microscope main objective system 316, through which a first observation beam path 328 and a second observation beam path 330 pass. The imaging optical unit 314 includes an output coupling beam splitter 326 arranged in the second optical observation beam path 330 on the side of the microscope main objective system 316 distant from the object region 332. The output coupling beam splitter 326 serves to decouple a first part of the observation light from the first observation beam path 328 and to feed it to an image acquisition assembly 336 in an image acquisition device 335 with an objective lens system 337 and an image sensor 338'. Moreover, a second part which differs from the first part of the observation light is also decoupled from the first observation beam path 328 by the output coupling beam splitter 326 in order to guide the second part to a further image acquisition assembly 340 in the image acquisition device 335.

The binocular tube 366 has a first display assembly 348 with a display 346 and a second display assembly 352 with a display 350. For the purposes of actuating the displays 346 and 350, there is an image processing and control device 354 in the surgical microscope 310, the image processing and control device being able to be connected to an external computer unit 345. Object region image data provided by the computer unit 345 can in this case be electronically superposed, at the correct position, onto the image of the object region shown in the eyepiece 322 by the display device 365.

In the surgical microscope 310, there is a position sensor 391, by which the azimuth angle φ of the position of the axis of symmetry 392 of the optical axes 393 and 394 of the third eyepiece 369 and of the fourth eyepiece 370 can be acquired in relation to the optical axis 395 of the microscope main objective system 316.

For the purposes of visualizing the images, acquired by the image acquisition assemblies 336 and 340, in the second optical observation beam path 330, which passes through the microscope main objective system 316, the surgical microscope 310 can be connected to an image reproduction device, preferably embodied as a 3D monitor, as alternative or in addition to the binocular tube 366 for the co-observation.

Figure 11:
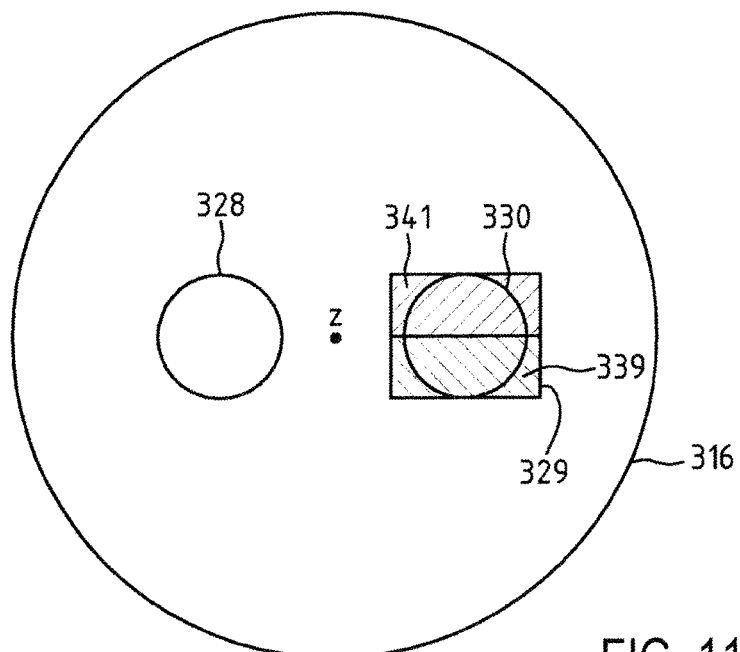
FIG. 11 shows a left-hand and right-hand stereoscopic observation beam path of the surgical microscope passing through the microscope main objective system.

FIG. 11 shows the first, left-hand stereoscopic optical observation beam path 328 and the second, right-hand stereoscopic optical observation beam path 330 of the surgical microscope 310 in the plane of the microscope main objective system 316. FIG. 11 moreover shows the perpendicular projection of the image sensors 338' and 338" onto the microscope main objective system 316 in the direction of the observation light fed to the image sensors 338' and 338" through the microscope main objective system 316 from the object region 332.

In the binocular tube 366, the image of the object region 332 acquired by the image sensor 338' is displayed in the third eyepiece 369 by the image processing and control device 354, the light of which image passes through the portion 339 of the beam splitter 326. The light which passes through the portion 341 of the beam splitter 329 and which is acquired by the image sensor 338" as a further image of the object region 332 can be visualized in the eyepiece 370 by the display device 352. In this way, it is possible to provide a stereoscopic image of the object region 323 in the binocular tube 366 for an observer.

Figure 12:
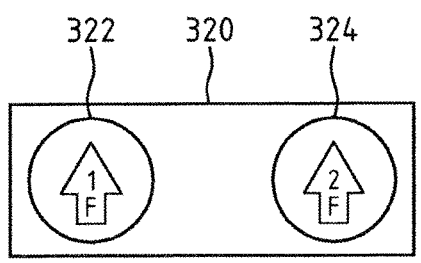
FIG. 12 shows the binocular vision in the binocular tube for the main observation and the binocular tube for the co-observation of the fourth surgical microscope.
Figure 12:
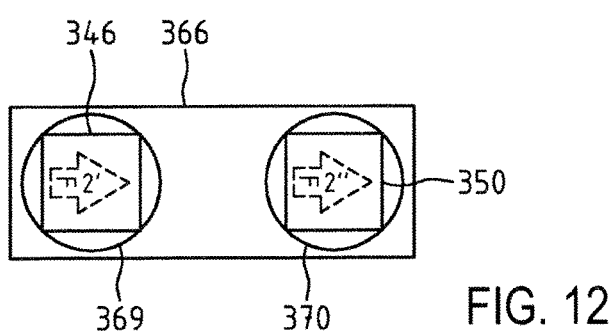

FIG. 12 shows the left-hand stereoscopic partial image 1 produced by an optical observation beam and the right-hand stereoscopic partial image 2 produced by an optical observation beam, this being perceived by an observer when looking into the first eyepiece 322 and second eyepiece 324 of the binocular tube 320 of a main observer. The left-hand stereoscopic partial image 2' produced by an optical observation beam and the right-hand stereoscopic partial image 2" produced by an optical observation beam, which in this case is perceived in the third and fourth eyepiece 369 and 370 of the binocular tube 366 by a co-observer as the image of the object region 332, has a perspective which corresponds to the perspective perceived by a main observer in the binocular tube 320. Here too, the co-observer stereo basis $B_{Co}$, which underlies the perspective vision in the binocular tube 366, is, however, smaller than the stereo basis $B_{Main}$ for the perspective vision in the binocular tube 320.

By virtue of the image processing and control device 354 in each case only feeding that image of the object region 332 to the display assemblies (348, 352) in the binocular tube 366 which is acquired with one of the two image acquisition assemblies (336, 340), a monoscopic image of the object region 332 can be displayed to an observer in the binocular tube 366. In this operating state of the surgical microscope 310, the azimuth angle φ acquired by the position sensor 391 is evaluated in the image processing and control device 354 in order to displace the image of the object region 332, displayed on the displays 346 and 350, in such a way that an observer perceives an object in the object region 332 with a natural visual impression in the binocular tube 366 when the azimuth angle φ is changed. This measure ensures that although the observer perceives the object in the object region monoscopically he or she can also perceive it in different viewing directions when the observer moves the binocular tube 366 about the optical axis 395 of the microscope main objective system 316.

Figure 13:
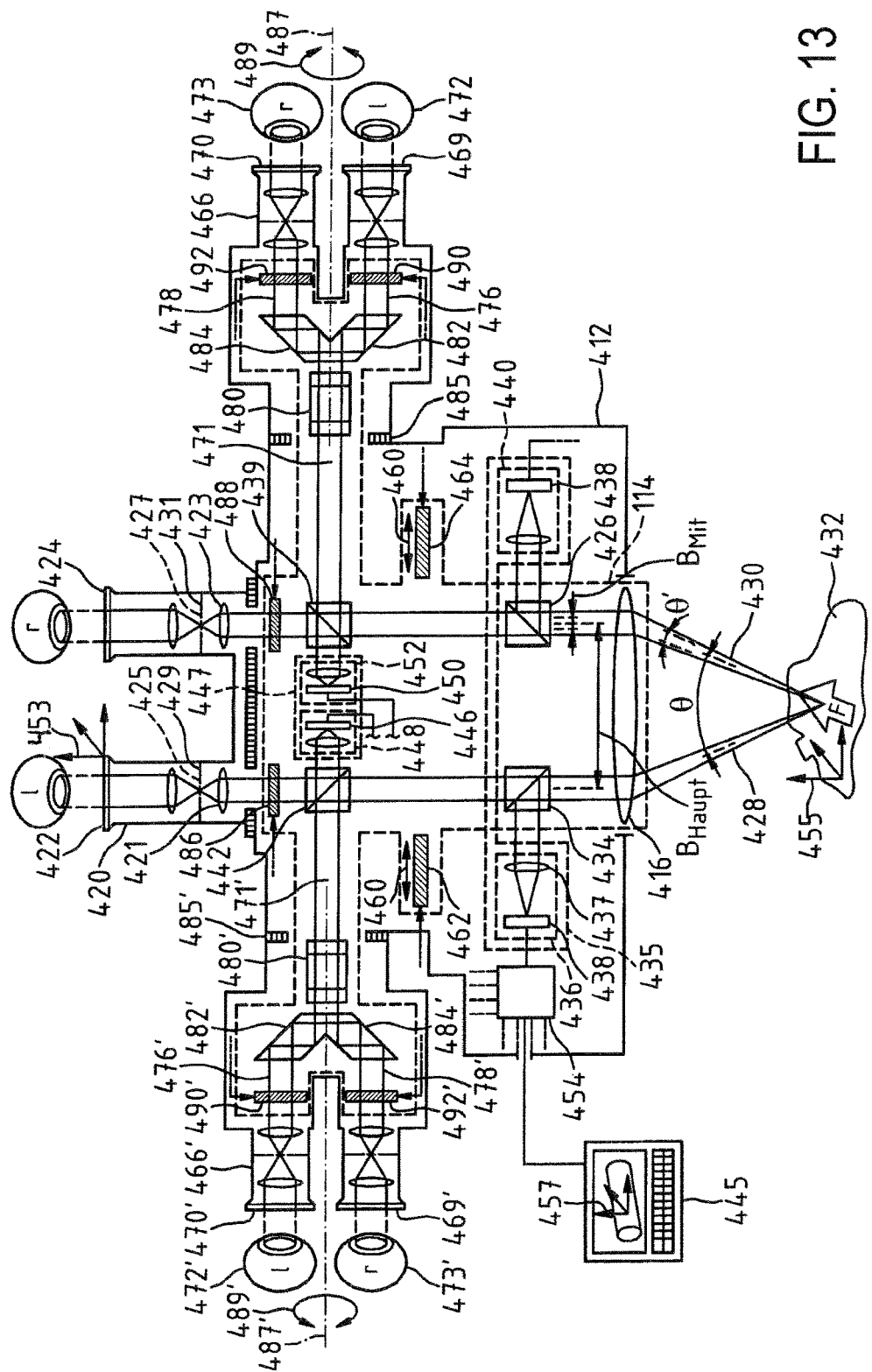
FIG. 13 shows a fifth surgical microscope for stereoscopic visualization of the object region in a first operating state including a binocular tube for the main observation and two binocular tubes for the co-observation.
Figure 14:
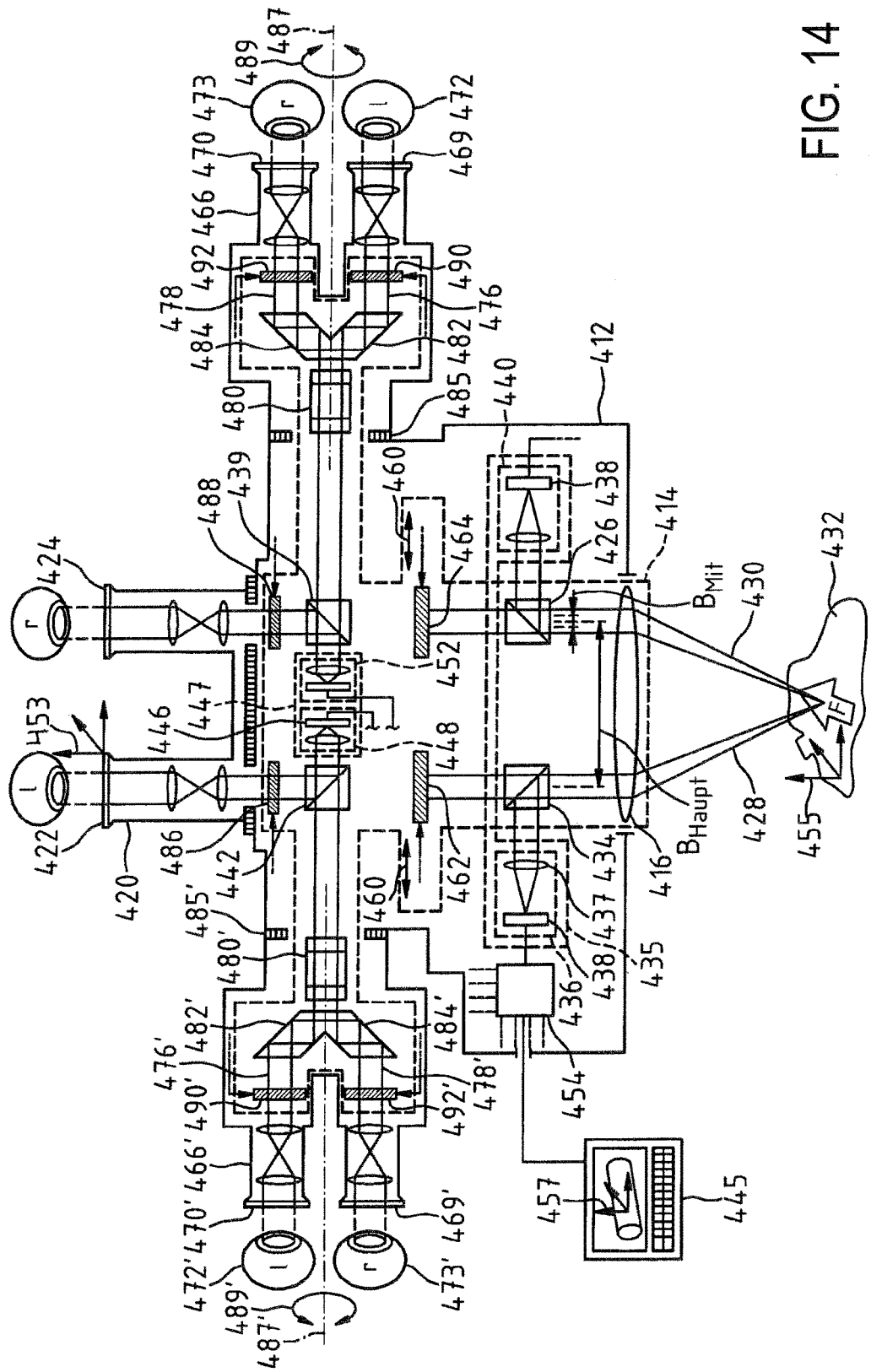
FIG. 14 shows the fifth surgical microscope in a second operating state.

FIG. 13 shows a fifth surgical microscope 410 for the stereoscopic visualization of the object region, including a binocular tube for the main observation and two binocular tubes for the co-observation, in a first operating state. In FIG. 14, the fifth surgical microscope is shown in a second operating state. The surgical microscope 410 has a binocular tube 420 for the main observation and it has two mutually opposing interfaces 485 and 485' for connecting a further binocular tube 466 and 466' for the preferably lateral co-observation.

To the extent that elements and the assemblies and beam paths in the surgical microscope 410 shown in FIG. 13 and FIG. 14 functionally correspond to the assemblies and beam paths in the surgical microscope 110 described on the basis of FIGS. 4 and 5 and to the elements shown in these figures, these are denoted in FIG. 13 and FIG. 14 by numbers as reference signs which have been increased by the number 300 in relation to FIG. 4.

The surgical microscope 410 includes a display device 447 with a first display assembly 448 and a second display assembly 452. The display assembly 448 includes a display, by which an image of the object region 432, acquired in the optical observation beam path 428 by the image acquisition assembly 436 of the image acquisition device 435, can be displayed in order to feed the image to the binocular tube 420 via the input coupling beam splitter 442 and to provide the image at the interface 485' for the binocular tube 466'.

Accordingly, there is a display in the display assembly 452, by which display an image of the object region 432, acquired in the optical observation beam path 430 by the image acquisition assembly 440 of the image acquisition device 435, can be displayed in order to feed the image to the binocular tube 420 via the input coupling beam splitter 439 and to provide the image at the interface 485 for the binocular tube 466.

In the surgical microscope 410, the displays in the display assemblies (448, 452) and the shutters 486, 488, 490, 492, 490', and 492' can be configured for comparatively short switching times in relation to the display and the shutters in the surgical microscope 110 described on the basis of FIG. 4 and FIG. 5.

It should be noted that the surgical microscope 410 can also, as a matter of principle, be embodied without the shutters 490, 490', 492, and 492' in the binocular tubes (466, 466') in a modified configuration. In this case, like in the surgical microscope 210, a monoscopic image of the object region 432 is displayed to an observer in the binocular tubes 466 and 466' when the first optical observation beam path 428 and the second optical observation beam path 430 are interrupted by the shutters 462 and 464.

Moreover, it should be noted that the surgical microscope 410 described above on the basis of FIG. 13 and FIG. 14 and the modified configurations thereof described above can, in principle, be embodied not only with two or more binocular tubes for the lateral co-observation but also with only one binocular tube, connected to the main body 412 of the surgical microscope 410, for the preferably lateral co-observation.

Figure 15:
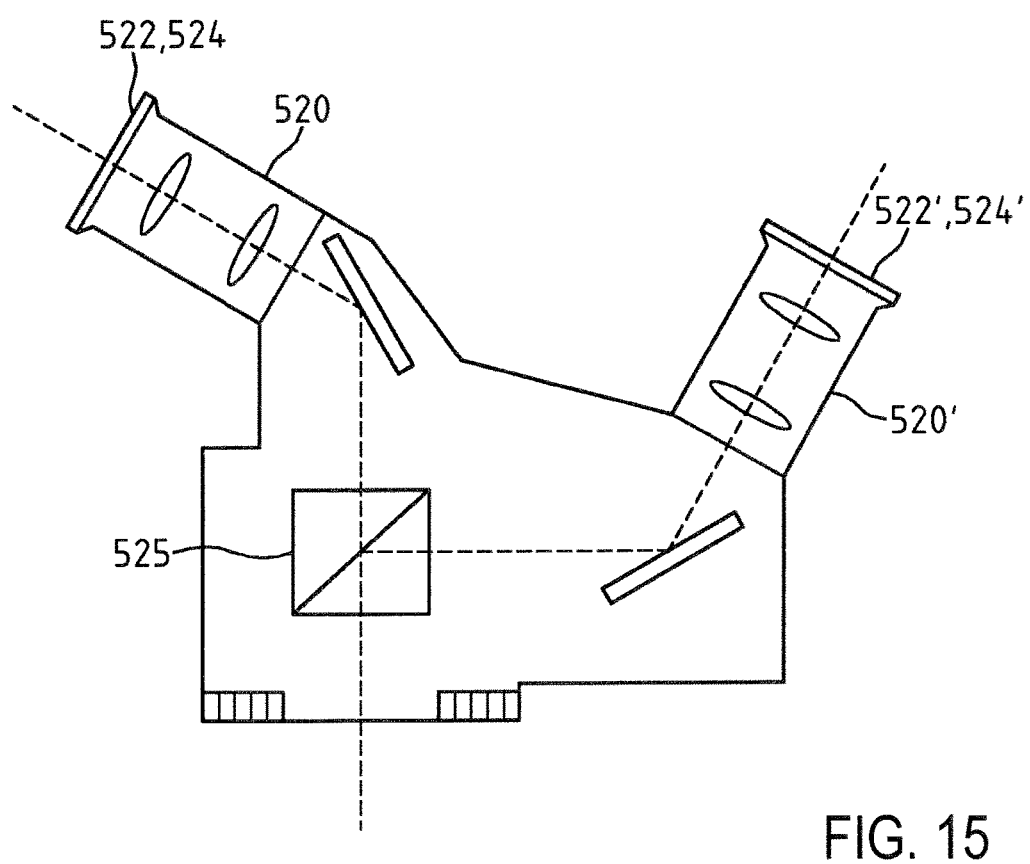
FIG. 15 shows two binocular tubes, arranged opposite to one another, for connection to the first, second, third, fourth or fifth surgical microscope.

FIG. 15 shows a tube assembly with two binocular tubes 520 and 520', arranged opposite one another, with eyepieces 522, 524 and 522', 524', which can be used in the first, second, third, fourth or fifth surgical microscope described above, in each case as an alternative to the binocular tube 20, 120, 220, 320 and 420, respectively. The tube assembly includes a beam splitter 525 for dividing a stereoscopic beam path, fed to the tube assembly, between the binocular tubes (520, 520').

It should be noted that the invention also extends to a surgical microscope, in which combinations of features from different exemplary embodiments described above can be found.

In summary, the following, in particular, should be noted: The invention relates to a surgical microscope 10, 110, 210, 310, and 410 for producing an observation image of an object region 32, 132, 232, 332, and 432 for an observer. The surgical microscope 10, 110, 210, and 410 has an image acquisition device 35, 135, 235, and 435 for acquiring an image of the object region 32, 132, 223, and 432 with a display device 47, 147, 247, and 447 and it has an image processing and control device 54, 154, 254, and 454, which is connected to the image acquisition device 35, 135, 235, 335, and 435 and to the display device 47, 147, 247, and 447 for visualizing an image of the object region 32, 132, 232, and 432 acquired by the image acquisition device 35, 135, 235, and 435. The surgical microscope 10, 110, 210, and 410 includes a computer unit 45, 145, 245, and 445, connected to the image processing and control device 54, 154, 254, and 454, for providing object region image data feedable by the display device 47, 147, 247, and 447 for the display and obtained in an imaging method. In the surgical microscope 10, 110, 210, and 410, there is a switchable imaging optical unit 14, 114, 214, and 414 which, in a first switching state, feeds the observation image of the object region 32, 132, 232, and 432 to an eyepiece 22, 122, 222, and 422 by an optical observation beam path 28, 128, 228, and 428, onto which the object region image data displayed by the display device 47, 147, 247, and 447 are superposable at the correct position. In a further switching state different from the first switching state, the switchable imaging optical unit 14, 114, 214, and 414 interrupts the purely optical observation beam path 28, 128, 228, and 428 from the object region 32, 132, 232, and 432 to the eyepiece 22, 122, 222, and 422 in order to display an image of the object region 32, 132, 232, and 432 from the optical observation beam path 28, 128, 228, and 428 in the eyepiece 22, 122, 222, and 422, the image being acquired by the image acquisition device 35, 135, 235, and 435 and displayed by the display device 47, 147, 247, and 447.

It is understood that the foregoing description is that of the preferred embodiments of the invention and that various changes and modifications may be made thereto without departing from the spirit and scope of the invention as defined in the appended claims.

LIST OF REFERENCE NUMERALS 1, 2, 2', 2" Partial image
10 Surgical microscope
12 Surgical microscope main body
14 Imaging optical unit
16 Microscope main objective system
18 Interface
20 Binocular tube
21, 23 Tube lens
22, 24 Eyepiece
25, 27 Intermediate image plane
26, 34 Output coupling beam splitter
28, 30 Observation beam path
29, 31 Ocular field stop
32 Object region
35 Image acquisition device
36 Image acquisition assembly
37 Objective lens system
38 Image sensor
40 Image acquisition assembly
42, 44 Input coupling beam splitter
45 Computer unit
46, 50 Display
47 Display device
48, 52 Display assembly
49, 51 Display lens
53, 55, 57 Coordinate system
54, 56 Image processing and control device
58 Image reproduction device
60 Double-headed arrow
62, 64 Shutter element
72, 74 Eye
110 Surgical microscope
112 Surgical microscope main body
114 Imaging optical unit
116 Microscope main objective system
118 Interface
120 Binocular tube
121, 123 Tube lens
122, 124 Eyepiece
125, 127 Intermediate image plane
126, 134 Output coupling beam splitter
128, 130 Observation beam path
129, 131 Ocular field stop
133 Optical axis
132 Object region
135 Image acquisition device
136 Image acquisition assembly
137 Objective lens system
138 Image sensor
139 Output coupling beam splitter
140 Image acquisition assembly
142 Input coupling beam splitter
145 Computer unit
146 Display
147 Display device
148 Display assembly
149, 151 Display lens
154 Image processing and control device
153, 155, 157 Coordinate system
160, 165 Double-headed arrow
162, 164, 167 Shutter element
166 Binocular tube
169, 170 Eyepiece
171 Beam path
172, 174 Left and right eye
176, 178 Observation beam path
180 Dove prism
182, 184 Pupil separation mirror system
186, 188,
190, 192 Shutter
187 Axis
189 Double-headed arrow
210 Surgical microscope
220 Binocular tube
221, 223 Tube lens
222, 224 Eyepiece
225, 227 Intermediate image plane
228, 230 Observation beam path
229, 231 Ocular field plane
232 Object region
235 Image acquisition device
236 Image acquisition assembly
237 Objective lens system
238 Image sensor
239 Output coupling beam splitter
240 Image acquisition assembly
242 Input coupling beam splitter
245 Computer unit
246 Display
247 Display device
248 Display assembly 249, 251 Display lens
253, 255, 257 Coordinate system
254 Image processing and control device
266 Binocular tube
269, 270 Eyepiece
276, 278 Observation beam path
280 Dove prism
282, 284 Pupil separation mirror system
286, 288,
290, 292, 293 Shutter
287 Axis
289 Double-headed arrow
310 Surgical microscope
312 Surgical microscope main body
314 Imaging optical unit
315 Display device
316 Microscope main objective system
318 Interface
320 Binocular tube
322, 324 Eyepiece
326 Output coupling beam splitter
328, 330 Observation beam path
332 Object region
335 Image acquisition device
336, 340 Image acquisition assembly
337 Objective lens system
338', 338" Image sensor
339, 341 Portion
367 Holding system
340 Image acquisition device
345 Computer unit
346, 350 Display
348, 352 Display assembly
354 Image processing and control device
353, 355, 357 Coordinate system
358 Visualization device
365 Display device
366 Binocular tube
367 Support system
369, 370 Eyepiece
372, 374 Left and right eye
391 Position sensor
392 Axis of symmetry
393, 394, 395 Optical axis
410 Surgical microscope
412 Surgical microscope main body
414 Imaging optical unit
416 Microscope main objective system
418 Interface
420 Binocular tube
421, 423 Tube lens
422, 424 Eyepiece
425, 427 Intermediate image plane
426, 434 Output coupling beam splitter
428, 430 Observation beam path
429, 431 Ocular field stop
433 Optical axis
432 Object region
435 Image acquisition device
436 Image acquisition assembly
437 Objective lens system
438 Image sensor
439 Output coupling beam splitter
440 Image acquisition assembly
442 Input coupling beam splitter
445 Computer unit
446 Display
447 Display device
448 Display assembly
449, 451 Display lens
450 Display
452 Display assembly
453, 455, 457 Coordinate system
454 Image processing and control device
460, 465 Double-headed arrow
462, 464, 467 Shutter element
466, 466' Binocular tube
469, 470,
469', 470' Eyepiece
471, 471' Beam path
472, 474,
472', 474' Left and right eye
476, 478,
476', 478' Observation beam path
480, 480' Dove prism
482, 484,
482', 484' Pupil separation mirror system
485, 485' Interface
486, 488,
490, 492,
490', 492' Shutter
487, 487' Axis
489, 489' Double-headed arrow
520, 520' Binocular tube
522, 524,
522', 524' Eyepiece
525 Beam splitter

What is claimed is:

1. A surgical microscope for generating an observation image of an object region for an observer, the surgical microscope comprising:

an image acquisition device configured to acquire an image of the object region;

a display device;

an image processing and control device connected to said image acquisition device and to said display device to visualize the image of the object region acquired by said image acquisition device;

a computer unit connected to said image processing and control device;

said computer unit being configured to provide object region image data to said display device to be displayed on said display device;

said object region image data being obtained by an imaging method;

a switchable imaging optical unit defining an optical observation beam path and having a first switching state and a second switching state;

an eyepiece;

said switchable imaging optical unit being configured to feed said observation image of the object region to said eyepiece via said optical observation beam path with said object region image data being superposable in a matching position onto said observation image of the object region when said switchable imaging optical unit is in said first switching state;

said switchable imaging optical unit being configured to interrupt said optical observation beam path between the object region and said eyepiece in order to display the image of the object region in said eyepiece that is acquired by said image acquisition device and displayed by said display device when said switchable imaging optical unit is in said second switching state; and, said image processing and control device being configured to electronically superpose the object region image data obtained by the imaging method and provided by the computer unit at the predefined position onto the image of the object region displayed by said display device in said eyepiece when said switchable imaging optical unit is in said second switching state.

2. A surgical microscope for generating an observation image of an object region for an observer, the surgical microscope comprising:
an image acquisition device configured to acquire an image of the object region;
a display device;
an image processing and control device connected to said image acquisition device and to said display device to visualize the image of the object region acquired by said image acquisition device;
a computer unit connected to said image processing and control device;
said computer unit being configured to provide object region image data to said display device to be displayed on said display device;
said object region image data being obtained by an imaging method;
a switchable imaging optical unit defining an optical observation beam path and having a first switching state and a second switching state;
an eyepiece;
said switchable imaging optical unit being configured to feed said observation image of the object region to said eyepiece via said optical observation beam path with said object region image data being superposable in a matching position onto said observation image of the object region when said switchable imaging optical unit is in said first switching state;
said switchable imaging optical unit being configured to interrupt said optical observation beam path between the object region and said eyepiece in order to display the image of the object region in said eyepiece that is acquired by said image acquisition device and displayed by said display device when said switchable imaging optical unit is in said second switching state; and,
said image processing and control device being configured to electronically superpose the object region image data obtained by the imaging method and provided by the computer unit at the predefined position onto the image of the object region displayed by said display device in said eyepiece when said switchable imaging optical unit is in said second switching state; wherein:
said eyepiece is a first eyepiece;
said optical observation beam path is a first optical observation beam path;
said switchable imaging optical unit further defines a second optical observation beam path;
said surgical microscope further comprises a second eyepiece for stereoscopic visualization with said first eye piece of a left-hand partial image and a right-hand partial image of the object region for the observer;
said switchable imaging optical unit is configured to feed the observation image of the object region to said second eyepiece via said second optical observation beam path when said switchable imaging optical unit is in said first switching state;
said switchable imaging optical unit being configured to interrupt said second optical observation beam path between the object region and said second eyepiece in order to display the image of the object region via said second optical observation beam path in said second eyepiece when said switchable imaging optical unit is in said second switching state; and,
said image is acquired by the image acquisition device and displayed by said display device.

3. The surgical microscope of claim 2, wherein:
said image processing and control device electronically superposes said object region image data at the predefined position onto the image of the object region displayed in said second eyepiece by said display device when said switchable imaging optical unit is in said second switching state; and,
said object region image data is provided by said computer unit and obtained by the imaging method.

4. The surgical microscope of claim 2, further comprising:
a third eyepiece configured to generate the observation image of the object region for a co-observer;
a third optical observation beam path;
said display device being a first display device;
a second display device;
said switchable imaging optical unit being configured to feed the observation image of the object region to said third eyepiece via said third optical observation beam path superposed onto said second optical observation beam path when said switchable imaging optical unit is in said first switching state;
said switchable imaging optical unit being configured to interrupt said third optical observation beam path between the object region and said third eyepiece in order to display the image of the object region from the first optical observation beam path or from the second optical observation beam path in said third eyepiece when said switchable imaging optical unit is in said second switching state; and,
said image being acquired by said image acquisition device and displayed by at least one of said first and second display devices.

5. The surgical microscope of claim 4, further comprising:
a fourth eyepiece arranged to visualize a left-hand partial image and a right-hand partial image of the object region for the co-observer;
a fourth optical observation beam path;
said switchable imaging optical unit being configured to feed the observation image of the object region to the fourth eyepiece via said fourth optical observation beam path superposed onto said second optical observation beam path when said switchable imaging optical unit is in said first switching state;
said switchable imaging optical unit being configured to interrupt said fourth optical observation beam path between the object region and said fourth eyepiece in order to display the image of the object region from the second optical observation beam path in the fourth eyepiece when said switchable imaging optical unit is in said second switching state; and,
said image being acquired by said image acquisition device and displayed by the at least one of said first and second display devices.

6. The surgical microscope of claim 5, further comprising:
a first time-sequentially actuatable shutter arranged in the third optical observation beam path;
a second time-sequentially actuatable shutter arranged in the fourth optical observation beam path;

said first and second time-sequentially actuatable shutters being coupled to a display of at least one of said first and second display devices so that:
a first partial image of the object region is visualized in the third eyepiece from the optical observation beam path by the display of the at least one of the first and second display devices when the first time-sequentially actuatable shutter unblocks the third observation beam path and the second shutter interrupts the fourth optical observation beam path; and,
a second partial image of the object region is visualized in the fourth eyepiece from the second optical observation beam path by the display of the at least one of the first and second display devices when the first time-sequentially actuatable shutter interrupts the third optical observation beam path and the second time-sequentially actuatable shutter unblocks the fourth observation beam path.

7. The surgical microscope of claim 4, further comprising:
a fourth eyepiece arranged to visualize a left-hand partial image and a right-hand partial image of the object region to the co-observer;
a fourth optical observation beam path;
said switchable imaging optical unit being configured to feed the observation image of the object region to said fourth eyepiece via said fourth optical observation beam path superposed onto said second optical observation beam path when said switchable imaging optical unit is in said first switching state;
said switchable imaging optical unit being configured to interrupt said fourth optical observation beam path between the object region and said fourth eyepiece in order to display the image of the object region from said first optical observation beam path or from said second optical observation beam path in said third eyepiece and in said fourth eyepiece; and,
said image being acquired by said image acquisition device and displayed by said at least one of said first and second display devices.

8. The surgical microscope of claim 4, further comprising:
a device for pupil separation;
said device for pupil separation being configured to divide a beam path decoupled from said second optical observation beam path into a first stereoscopic partial beam path and a second stereoscopic partial beam path;
said first stereoscopic partial beam path being configured to be feedable to said third eyepiece as said third optical observation beam path; and,
said second stereoscopic partial beam path being configured to be feedable to said fourth eyepiece as said fourth optical observation beam path.

9. The surgical microscope of claim 4, wherein:
said image processing and control device is configured to electronically superpose said object region image data at said predefined position onto the image of the object region displayed by said at least one of said first and second display devices; and,
said object region image data being provided by said computer unit and obtained by said imaging method.

* * * * *